United States Patent
Song et al.

(10) Patent No.: US 11,053,468 B2
(45) Date of Patent: *Jul. 6, 2021

(54) MULTIWELL CELL CULTURE SYSTEM HAVING ROTATING SHAFTS FOR MIXING CULTURE MEDIA AND METHOD OF USE THEREOF

(71) Applicant: The Johns Hopkins University, Baltimore, MD (US)

(72) Inventors: Hongjun Song, Clarksville, MD (US); Guoli Ming, Clarksville, MD (US); Mingxi Max Song, Clarksville, MD (US); Christopher Hadiono, Armonk, NY (US); William Jeang, Houston, TX (US); Ha Nam Nguyen, Baltimore, MD (US); Xuyu Qian, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/804,924

(22) Filed: Feb. 28, 2020

(65) Prior Publication Data
US 2020/0208090 A1    Jul. 2, 2020

Related U.S. Application Data

(62) Division of application No. 15/775,368, filed as application No. PCT/US2016/061610 on Nov. 11, 2016, now Pat. No. 10,597,623.
(Continued)

(51) Int. Cl.
*C12M 1/32*     (2006.01)
*B01F 7/18*     (2006.01)
(Continued)

(52) U.S. Cl.
CPC ......... *C12M 23/12* (2013.01); *B01F 7/00133* (2013.01); *B01F 7/00141* (2013.01);
(Continued)

(58) Field of Classification Search
CPC ...... C12M 23/12; C12M 41/36; C12M 27/02; C12M 41/48; C12M 27/10; C12M 25/06;
(Continued)

(56) References Cited

U.S. PATENT DOCUMENTS

| 445,703 A * | 2/1891 | Parry ....................... B03B 9/00 209/2 |
| 1,842,938 A * | 1/1932 | Hancock ............... B01F 7/1695 366/251 |

(Continued)

FOREIGN PATENT DOCUMENTS

WO    2015/189577 A1 * 12/2015

OTHER PUBLICATIONS

Sun, et al., A Miniaturized Bioreactor System for the Evaluation of Cell Interaction With Designed Substrates in Perfusion Culture. J Tissue Eng Regen Med. Dec. 2012;6 Suppl 3:s4-14.
(Continued)

*Primary Examiner* — Charles Cooley
(74) *Attorney, Agent, or Firm* — DLA Piper LLP (US)

(57) ABSTRACT

A method of cell culture and a method of generating organoids is provided. The methods utilize a cell culture system which includes a multiwell culture plate having shafts for mixing culture media within wells of the culture plate. The multiwell culture plate includes a base substrate having a plurality of culture wells, and a shaft operably associated with each culture well, each shaft being configured to mix media present in each culture well and having a gear adapted to operably associate with a gear on a shaft associated with an adjacent culture well. The system further
(Continued)

includes a motor having a drive shaft in operable communication with the shaft gears of the multiwell culture plate. The system can be widely used as a standard platform to generate stem cell-derived human organoids for any tissue and for high-throughput drug screenings, toxicity testing, and modeling normal human organ development and diseases.

19 Claims, 15 Drawing Sheets

Specification includes a Sequence Listing.

Related U.S. Application Data

(60) Provisional application No. 62/254,943, filed on Nov. 13, 2015.

(51) Int. Cl.

| | | |
|---|---|---|
| B01F 13/10 | (2006.01) | |
| C12M 1/34 | (2006.01) | |
| C12M 1/06 | (2006.01) | |
| B01F 15/00 | (2006.01) | |
| B01F 7/00 | (2006.01) | |
| C12M 1/36 | (2006.01) | |
| C12M 3/00 | (2006.01) | |
| C12M 1/12 | (2006.01) | |
| C12M 3/04 | (2006.01) | |
| C12N 5/0793 | (2010.01) | |
| G01N 33/50 | (2006.01) | |

(52) U.S. Cl.
CPC ............ *B01F 7/18* (2013.01); *B01F 13/1022* (2013.01); *B01F 15/00454* (2013.01); *C12M 21/08* (2013.01); *C12M 25/06* (2013.01); *C12M 27/02* (2013.01); *C12M 27/10* (2013.01); *C12M 41/36* (2013.01); *C12M 41/48* (2013.01); *C12N 5/0619* (2013.01); *G01N 33/5058* (2013.01); *G01N 33/5082* (2013.01); *B01F 2015/00623* (2013.01); *B01F 2215/0481* (2013.01)

(58) Field of Classification Search
CPC ................ C12M 21/08; B01F 7/00133; B01F 15/00454; B01F 13/1022; B01F 7/00141; B01F 7/18; B01F 2215/0481; B01F 2015/00623; B01F 13/1013; G01N 33/5082; G01N 33/5058; C12N 5/0619
USPC .................................................. 366/198, 291
See application file for complete search history.

(56) References Cited

U.S. PATENT DOCUMENTS

| | | | | |
|---|---|---|---|---|
| 1,911,644 | A * | 5/1933 | Overbury | B01F 3/0853 |
| | | | | 366/172.1 |
| 2,526,351 | A * | 10/1950 | Grubelic | B01F 7/1695 |
| | | | | 366/198 |
| 5,587,298 | A * | 12/1996 | Horigane | C12M 27/00 |
| | | | | 366/300 |
| 5,697,703 | A * | 12/1997 | Lucchetti | B01F 7/1695 |
| | | | | 366/198 |
| 9,616,398 | B2 * | 4/2017 | Chien | B01F 7/005 |
| 10,597,623 | B2 * | 3/2020 | Song | B01F 7/00141 |
| 2004/0031333 | A1 * | 2/2004 | Buckner, III | B01F 7/0015 |
| | | | | 73/863 |
| 2005/0232074 | A1 * | 10/2005 | Higashihara | B01F 7/00166 |
| | | | | 366/273 |
| 2012/0067147 | A1 * | 3/2012 | Huang | B01F 7/00275 |
| | | | | 74/409 |
| 2013/0126436 | A1 * | 5/2013 | Ok | B03C 1/30 |
| | | | | 210/695 |
| 2015/0283524 | A1 * | 10/2015 | Chien | B01F 7/005 |
| | | | | 366/272 |
| 2017/0113197 | A1 * | 4/2017 | Middleton | B01F 7/00166 |
| 2018/0008944 | A1 * | 1/2018 | Ozeki | G01N 1/38 |
| 2018/0334646 | A1 * | 11/2018 | Song | B01F 7/18 |
| 2018/0345237 | A1 * | 12/2018 | Chien | B01F 13/08 |

OTHER PUBLICATIONS

Heymann, et al., Zika virus and microcephaly: why is this situation a PHEIC? Lancet 387, 719-721 (2016).
Rasmussen, et al., Zika Virus and Birth Defects—Reviewing the Evidence for Causality. N Engl J Med 374, 1981-1987 (2016).
Tang, et al., Zika Virus Infects Human Cortical Neural Progenitors and Attenuates Their Growth. Cell Stem Cell 18, 587-590 (2016).
Dang, et al., Zika Virus Depletes Neural Progenitors in Human Cerebral Organoids through Activation of the Innate Immune Receptor TLR3. Cell Stem Cell 19, 258-265 (2016).
Li, et al., Zika Virus Disrupts Neural Progenitor Development and Leads to Microcephaly in Mice. Cell Stem Cell 19, 120-126 (2016).
Cugola, et al., The Brazilian Zika virus strain causes birth defects in experimental models. Nature 534, 267-271 (2016).
Liang, et al., Zika Virus NS4A and NS4B Proteins Deregulate Akt-mTOR Signaling in Human Fetal Neural Stem Cells to Inhibit Neurogenesis and Induce Autophagy. Cell Stem Cell, (2016).
Onorati, et al., Zika Virus Disrupts Phospho-TBK1 Localization and Mitosis in Human Neuroepithelial Stem Cells and Radial Glia. Cell Rep, (2016).
Zhang, et al., Molecular signatures associated with ZIKV exposure in human cortical neural progenitors. Nucleic Acids Res, (2016).
Yoon, et al., Modeling a genetic risk for schizophrenia in iPSCs and mice reveals neural stem cell deficits associated with adherens junctions and polarity. Cell Stem Cell 15, 79-91 (2014).
Gotz, et al. The cell biology of neurogenesis. Nature reviews. Molecular cell biology 6, 777-788 (2005).
Brault, et al., Comparative Analysis Between Flaviviruses Reveals Specific Neural Stem Cell Tropism for Zika Virus in the Mouse Developing Neocortex. EBioMedicine 10, 71-76 (2016).
Wu, et al., Vertical transmission of Zika virus targeting the radial glial cells affects cortex development of offspring mice. Cell research 26, 645-654 (2016).
Wu, et al., Scanning mutagenesis studies reveal a potential intramolecular interaction within the C-terminal half of dengue virus NS2A involved in viral RNA replication and virus assembly and secretion. J Virol 89, 4281-4295 (2015).
Xie, et al., Two distinct sets of NS2A molecules are responsible for dengue virus RNA synthesis and virion assembly. J Virol 89, 1298-1313 (2015).
Leung, et al., Role of nonstructural protein NS2A in flavivirus assembly. J Virol 82, 4731-4741 (2008).
Jeong, et al., Rapid identification of monospecific monoclonal antibodies using a human proteome microarray. Mol Cell Proteomics 11, O111 016253 (2012).
Oldenburg, et al., VASP, zyxin and TES are tension-dependent members of Focal Adherens Junctions independent of the alpha-catenin-vinculin module. Scientific reports 5, 17225 (2015).
Serrels, et al., Src/FAK-mediated regulation of Ecadherin as a mechanism for controlling collective cell movement: insights from in vivo imaging. Cell Adh Migr 5, 360-365 (2011).
Rasin, et al., Numb and Numbl are required for maintenance of cadherin-based adhesion and polarity of neural progenitos. Nat Neurosci 10, 819-827 (2007).
Tang, et al., Smad7 stabilizes beta-catenin binding to Ecadherin complex and promotes cell-cell adhesion, J Biol Chem 283, 23956-23963 (2008).
Cui, et al., Application of multiple parallel perfused microbioreactors and three-dimensional stem cell culture for toxicity testing. Toxicology in Vitro 2007;21(7):1318-1324.

(56) References Cited

OTHER PUBLICATIONS

Wang, et al., Crucial roles of the Arp2/3 complex during mammalian corticogenesis. Development 143, 2741-2752 (2016).
Rakic, et al., Elusive radial glial cells: historical and evolutionary perspective. Glia 43, 19-32 (2003).
Buchman, et al., Spindle regulation in neural precursors of flies and mammals. Nat Rev Neurosci 8, 89-100 (2007).
Bultje, et al., Mammalian Par3 regulates progenitor cell asymmetric division via notch signaling in the developing neocortex. Neuron 63, 189-202 (2009).
Stocker, et al., The role of adherens junctions in the developing neocortex. Cell Adh Migr 9, 167-174 (2015).
Cappello, et al., The Rho-GTPase cdc42 regulates neural progenitor fate at the apical surface. Nat Neurosci 9, 1099-1107 (2006).
Yokota, et al., The adenomatous polyposis coli protein is an essential regulator of radial glial polarity and construction of the cerebral cortex. Neuron 61, 42-56 (2009).
Zhang, et al., Cortical neural precursors inhibit their own differentiation via N-cadherin maintenance of beta-catenin signaling. Developmental cell 18, 472-479 (2010).
Chen, et al., Coupling assembly of the E-cadherin/beta-catenin complex to efficient endoplasmic reticulum exit and basal-lateral membrane targeting of Ecadherin in polarized MDCK cells. J Cell Biol 144, 687-699 (1999).
Harris, et al., Adherens junctions: from molecules to morphogenesis. Nature reviews. Molecular cell biology 11, 502-514 (2010).
Wahl, et al., N-cadherin-catenin complexes form prior to cleavage of the proregion and transport to the plasma membrane. J Biol Chem 278, 17269-17276 (2003).
Mlakar, et al., Zika Virus Associated with Microcephaly. N Engl J Med 374, 951-958 (2016).
Sir, et al., A primary microcephaly protein complex forms a ring around parental centrioles. Nat Genet 43, 1147-1153 (2011).
Gilmore, et al., Genetic causes of microcephaly and lessons for neuronal development. Wiley Interdiscip Rev Dev Biol 2, 461-478 (2013).
Pylro, et al., ZIKV—CDB: A Collaborative Database to Guide Research Linking SncRNAs and ZIKA Virus Disease Symptoms. PLoS Negl Trop Dis 10, e0004817 (2016).
Chiang, et al., Integration-free induced pluripotent stem cells derived from schizophrenia patients with a DISC1 mutation. Mol Psychiatry 16, 358-360 (2011).
Saito, et al., In vivo electroporation in the embryonic mouse central nervous system. Nat Protoc 1, 1552-1558 (2006).
Wada, et al., SSR alpha and associated calnexin are major calcium binding proteins of the endoplasmic reticulum membrane. J Biol Chem 266, 19599-19610 (1991).
Zhu, et al., Global analysis of protein activities using proteome chips. Science 293, 2101-2105 (2001).
Hu, et al., DNA methylation presents distinct binding sites for human transcription factors. eLife 2, e00726 (2013).
Szklarczyk, et al., String v10: protein-protein interaction networks, integrated over the tree of life. Nucleic Acids Res 43, D447-452 (2015).
Shannon, et al., Cytoscape: a software environment for integrated models of biomolecular interaction networks. Genome research 13, 2498-2504 (2003).
Huang, et al., Systematic and integrative analysis of large gene lists using DAVID bioinformatics resources. Nat Protoc 4, 44-57 (2009).
Currle, et al., Culture of mouse neural stem cell precursors. J Vis Exp, 152 (2007).
Wen, et al., Synaptic dysregulation in a human iPS cell model of mental disorders. Nature 515, 414-418 (2014).
Lancaster, et al., Cerebral Organoids Model Human Brain Development and Microcephaly. Nature 501, 373-379 (2013).
Gelinsky, et al., Bioreactors in tissue engineering: Advances in stem cell culture and three-dimensional tissue constructs. Eng Life Sci 2015; 15: 670-677.
Liu, et al., Stem cell engineering in bioreactors for large-scale bioprocessing. Eng Life Sci 2014; 14:4-15.

* cited by examiner

SEQUENCE LISTING

<160> NUMBER OF SEQ ID NOS: 14

<210> SEQ ID NO 1
<211> LENGTH: 24
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 1
tcaacagcaa ctcccactct tcca                                          24

<210> SEQ ID NO 2
<211> LENGTH: 24
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 2
accctgttgc tgtagccgta ttca                                          24

<210> SEQ ID NO 3
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 3
tcaagaggct gtgttgctgt                                               20

<210> SEQ ID NO 4
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 4
caggctccag aagaagttgg                                               20

<210> SEQ ID NO 5
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 5
acagggtgct attccacgac                                              20

<210> SEQ ID NO 6
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 6
ctgcacaaac aatggaatgg                                              20

<210> SEQ ID NO 7
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 7
tccgtgaagt ctgtcctgtg                                              20

<210> SEQ ID NO 8
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 8
gcctctcacc agagtccttg                                              20

<210> SEQ ID NO 9
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 9
gggccatctc aactcctgta                                              20

<210> SEQ ID NO 10
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 10
gggacaggaa cactgcaaat                                              20

<210> SEQ ID NO 11
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 11

```
gggacaggaa cactgcaaat                                                   20

<210> SEQ ID NO 12
<211> LENGTH: 21
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 12
cggttgatgg tccagtttct t                                                 21

<210> SEQ ID NO 13
<211> LENGTH: 20
<212> TYPE: DNA
<213> ORGANISM: Homo sapiens
<220> FEATURE:
<221> NAME/KEY: misc_feature
<223> OTHER INFORMATION: Forward 5 primer used for quantitative PCR

<400> SEQUENCE: 13
ggctacttgt ggagggatca                                                   20

<210> SEQ ID NO 14
<211> LENGTH: 20
<212> TYPE: DNA
<213> ORGANISM: Homo sapiens
<220> FEATURE:
<221> NAME/KEY: misc_feature
<223> OTHER INFORMATION: Reverse 5 primer used for quantitative PCR

<400> SEQUENCE: 14
accctcacag ctgtcaatcc                                                   20
```

MULTIWELL CELL CULTURE SYSTEM HAVING ROTATING SHAFTS FOR MIXING CULTURE MEDIA AND METHOD OF USE THEREOF

CROSS-REFERENCE TO RELATED APPLICATIONS

This application a divisional application of U.S. application Ser. No. 15/775,368 filed Oct. 5, 2018, issued as U.S. Pat. No. 10,597,623; which is a 35 USC § 371 National Stage application of International Application No. PCT/US2016/061610 filed Nov. 11, 2016, now expired; which claims the benefit under 35 USC § 119(e) to U.S. Application Ser. No. 62/254,943 filed Nov. 13, 2015. The disclosure of each of the prior applications is considered part of and is incorporated by reference in the disclosure of this application.

STATEMENT REGARDING FEDERALLY SPONSORED RESEARCH OR DEVELOPMENT

This invention was made with government support under Grant Nos. NS048271, NS095348, MH105128, NS047344, NS097206 and MH106434 awarded by the National Institutes of Health. The government has certain rights in the invention.

INCORPORATION OF SEQUENCE LISTING

The material in the accompanying sequence listing is hereby incorporated by reference into this application. The accompanying sequence listing text file, named JHU3950-2_ST25, was created on Feb. 27, 2020 and is 4 KB in size. The file can be accessed using Microsoft Word on a computer that uses Windows OS.

BACKGROUND OF THE INVENTION

Field of the Invention

The present invention relates generally to cell culture, and more particularly to a cell culture system for three dimensional cell culture, and methods of use thereof.

Background Information

Spinning bioreactors have been used for three-dimensional (3D) cell culture and generation of organ-like tissues (organoids). The circular flow facilitates diffusion of oxygen and nutrients into cultured tissues, which enables non-attached suspension cultures to self-organize into 3D aggregates, which recapitulate in vivo environments better than traditional two-dimensional (2D) cultures. In addition, the shear stress generated from the fluid flow is a mechanical cue to regulate cell growth and differentiation. The use of spinning bioreactors has been shown to promote the formation of continuous cerebral tissues derived from human stem cells.

However, the spinning bioreactor products currently available on the market (e.g., the Corning® disposable spinner flasks), have several design features that limit its use. First, the flasks are large and require a significant amount of space within the standard size incubators used in most labs, i.e., only 6-10 bioreactors can fit into a single incubator on top of separate magnetic stirrer plates to activate the spinning mechanism. Second, the flasks require a large volume of cell culture media, ~50 to 200 mL, which can be extremely costly. Third, each flask can be used for only one culture condition. Thus, applications that require parallel cultures to test multiple conditions, such as toxin and drug screening, cannot be effectively conducted in these bulky flask systems.

Animal studies are costly, and typically long and controversial. Of even greater concerns are validity problems in cross-species extrapolation. Although physiologically more relevant than in vitro models, animal studies allow limited control of individual variables. As such, it is often difficult to extract specific information from the experiments. On the other hand, standard in vitro models are usually too simplistic in design. Therefore, there is a need for 'bridging the gap' between in vivo and in vitro studies through a more representative cellular environment, such as utilization of organoid structures that mimic living tissue. Although these microphysiological systems are still at their infancy, they have tremendous potential to transform basic biomedical research and drug discovery, since they can serve as a first step before clinical trials.

As such, there exists a need for more advanced platforms to perform meaningful biomedical research, such as innovate culture systems that overcome the deficiencies of conventional culture systems.

SUMMARY OF THE INVENTION

The present invention is based in part on the discovery of significant improvements to cell culture systems and methods of generating cultured organoids.

In one aspect, the invention provides a cell culture system. The system includes a standard multiwell culture plate which has a base substrate having a plurality of culture wells. Spinner shafts are associated with each culture well, each shaft being configured to mix media present in each culture well and having a gear adapted to operably associate with a gear on a shaft associated with an adjacent culture well. The system further includes a motor having a drive shaft in operable communication with the shaft gears, wherein rotation of the drive shaft causes rotation of each shaft and mixing of the media in each culture well at the same speed. In embodiments, each shaft is disposed in a cover plate overlying the base substrate. The cell culture system may further include multiple multiwell culture plates, the plates being stackable and having shafts driven by a single motor to have identical condition for the whole unit.

In another aspect, the invention provides a method of cell culture. The method includes providing a cell culture system of the invention, and culturing cells in a culture well in culture media under conditions suitable for cell culture, wherein the conditions comprise mixing of the cell culture via actuation of the motor, thereby culturing the cells.

In yet another aspect, the invention provides a method of producing organoids. The method includes providing a cell culture system of the present invention, culturing cells in a culture well in culture media under conditions suitable for cell culture, wherein the conditions comprise mixing of the cell culture via actuation of the motor, and harvesting organoids from the culture well, thereby producing organoids.

In still another aspect, the invention provides a method of screening an agent. The method includes providing a cell culture system of the present invention, culturing cells in a culture well in culture media under conditions suitable for cell culture, wherein the conditions comprise mixing of the cell culture via actuation of the motor, and introducing a biological agent into the culture media and detecting a cellular response, thereby screening the agent.

In another aspect, the invention provides a method of performing a biological assay. The method includes generating an organoid using the cell culture system of the present invention; contacting the organoid with a virus; and detecting infectivity of the virus, thereby performing a biological assay. In embodiments, the method further includes contacting the organoid with a biological agent and detecting a cellular response.

In still another aspect, the invention provides an organoid produced by the method of the invention. In some embodiments, the organoid is infected with a virus and suitable for use as a biological model for conducting an assay, for example, viral research.

In another aspect, the invention provides a method for treating a disease or disorder in a subject. In embodiments, the method includes administering or contacting the subject with an organoid generated utilizing the method or system of the invention.

In another aspect, the invention provides a kit for cell culture. The kit includes a cell culture system of the present invention, cell culture reagents, instructions for conducting cell culture utilizing the cell culture reagents, and optionally cells.

DETAILED DESCRIPTION OF THE INVENTION

The present invention is based in part on the discovery of significant improvements to cell culture systems and methods. The system provides a novel spinning bioreactor platform, referred to herein as SpinΩ, for higher-throughput 3D culturing of cells, such as stem cells (e.g., human induced pluripotent stem cells (iPSCs) or embryonic stem cells (ESCs)). SpinΩ is a miniaturized, motorized, and modular system that uses standard multi-well tissue culture plates. This small-scale format bioreactor greatly reduces the cost of generating organoids by reducing the amount of media required and incubator space needed. SpinΩ can be widely used as a standard platform to generate stem cell-derived human or animal organoids for any tissue and for high-throughput drug screenings, toxicity testing, and modeling normal human and animal organ development and diseases.

Before the present compositions and methods are described, it is to be understood that this invention is not limited to particular compositions, methods, and experimental conditions described, as such compositions, methods, and conditions may vary. It is also to be understood that the terminology used herein is for purposes of describing particular embodiments only, and is not intended to be limiting, since the scope of the present invention will be limited only in the appended claims.

As used in this specification and the appended claims, the singular forms "a", "an", and "the" include plural references unless the context clearly dictates otherwise. Thus, for example, references to "the method" includes one or more methods, and/or steps of the type described herein which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described.

Growing stem cells in 3-Dimensional culture can produce organoids that can recapitulate human tissues development in vitro. However, the current techniques to generate human organoids from stem cells are not robust, inefficient and variable. The present invention provides an innovative spin bioreactor, referred to herein as SpinΩ, for 3D culture of human induced pluripotent stem cells (iPSCs) to form organ-like tissues. SpinΩ is a miniaturized self-driven system that allows simultaneous spinning in standard multi-well tissue culture plates, offering suitable environment for 3D tissue culture. SpinΩ has been used to successfully generate human iPSC-derived tissues, such as cerebral cortex, midbrain and hypothalamus tissues, and as a high-throughput platform for environmental toxin testing.

Figure 1:
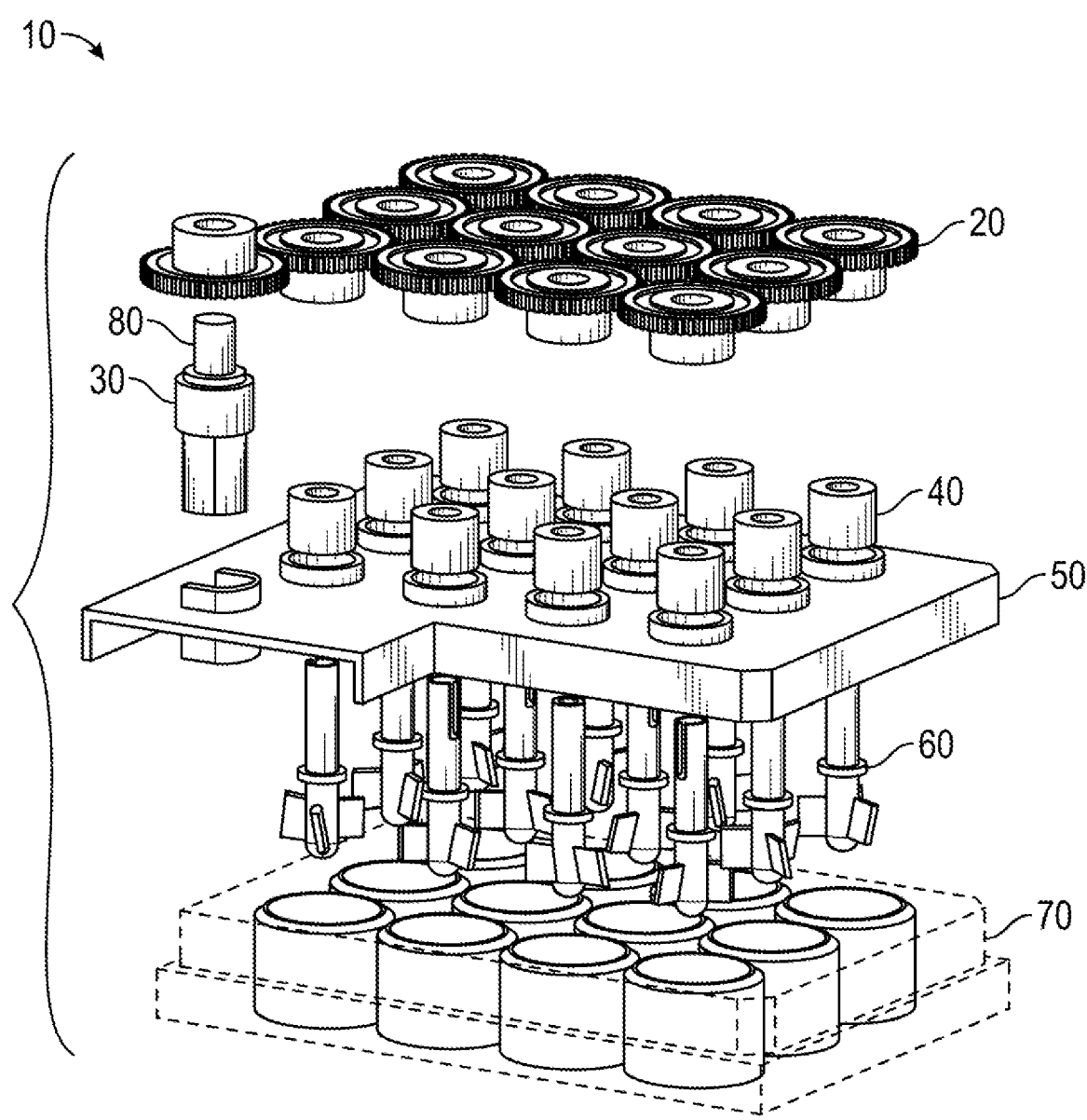
FIG. 1 is an expanded schematic of a cell culture system in one embodiment of the invention.
Figure 2A:
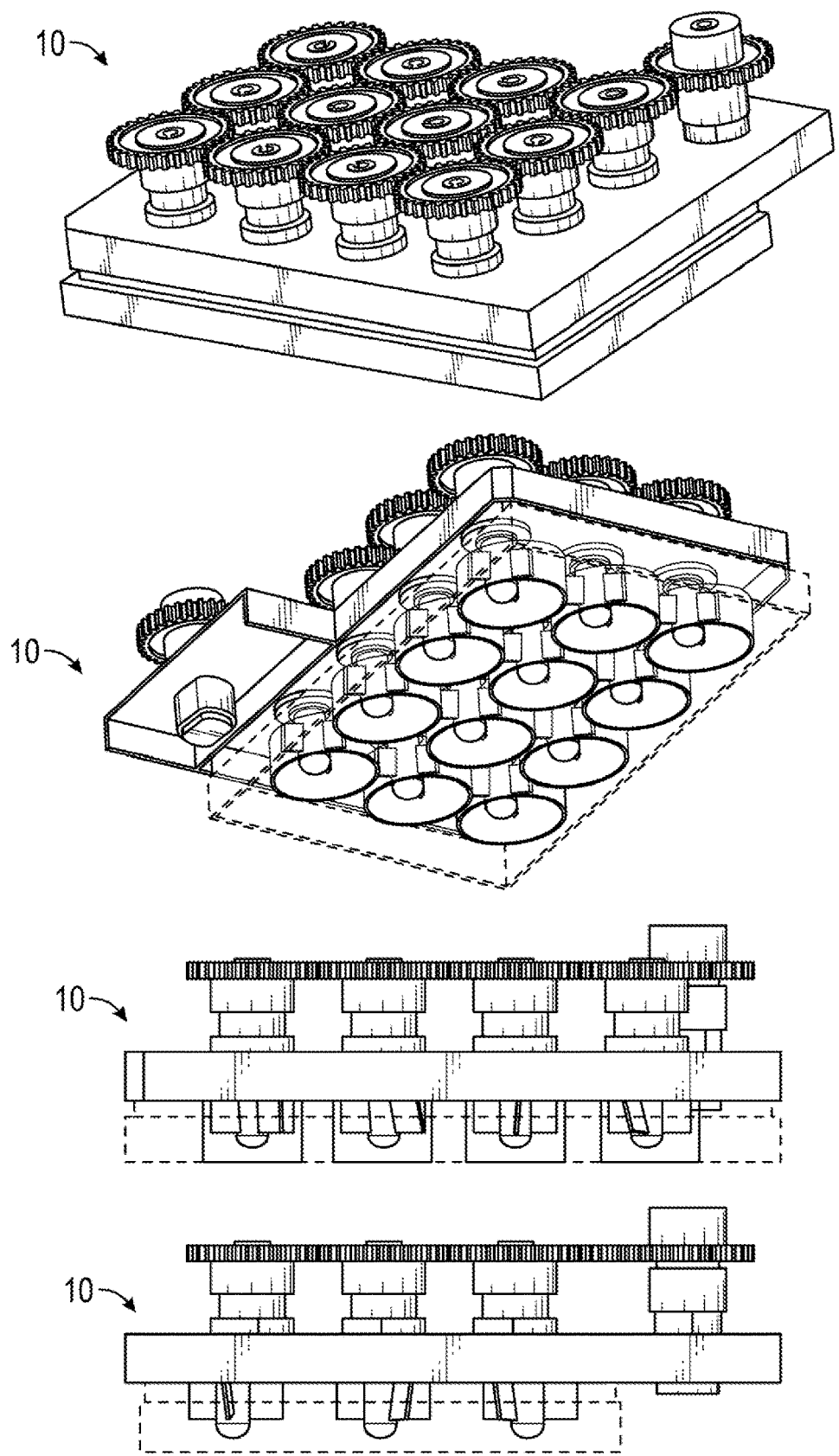
FIG. 2A is a series of perspective views of a cell culture system in embodiments of the invention.
Figure 2B:
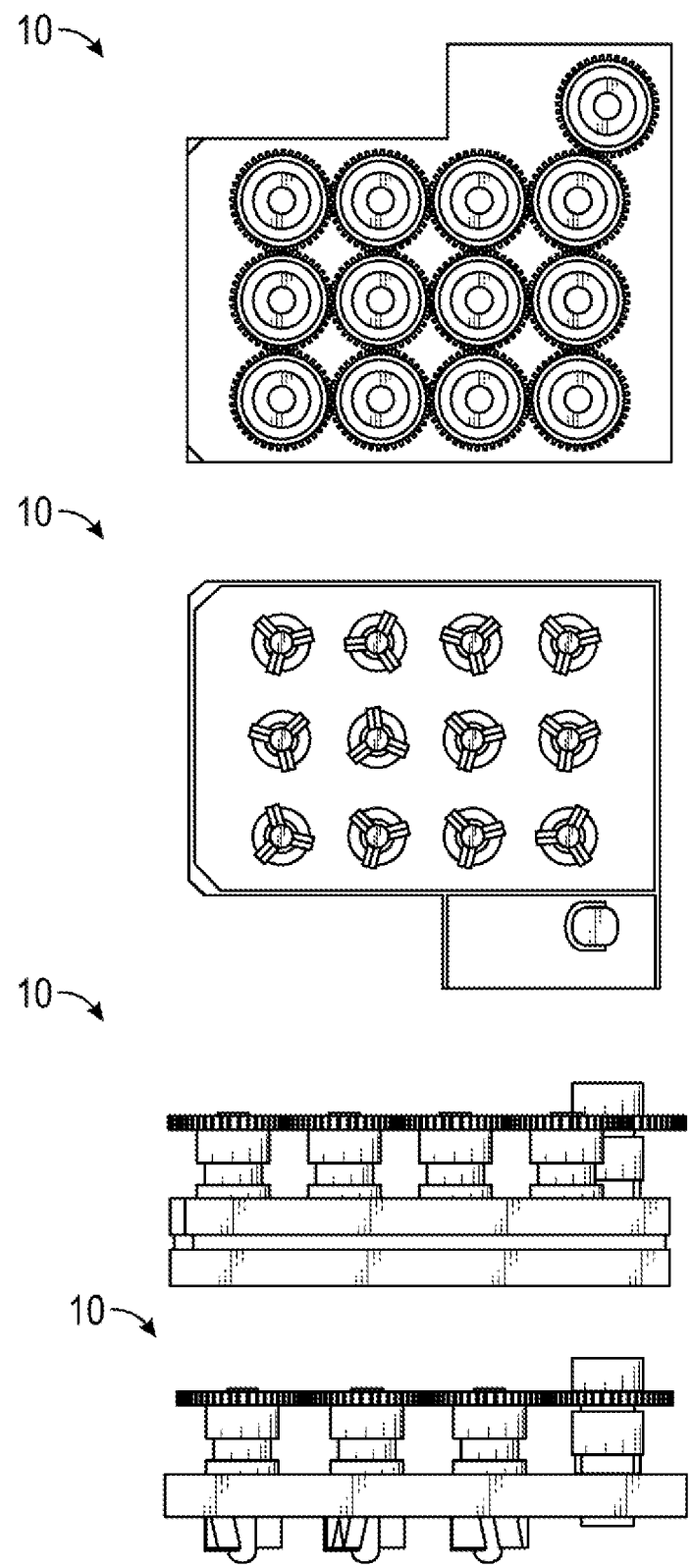
FIG. 2B is a series of different images of the cell culture system of FIG. 2A.
Figure 2C:
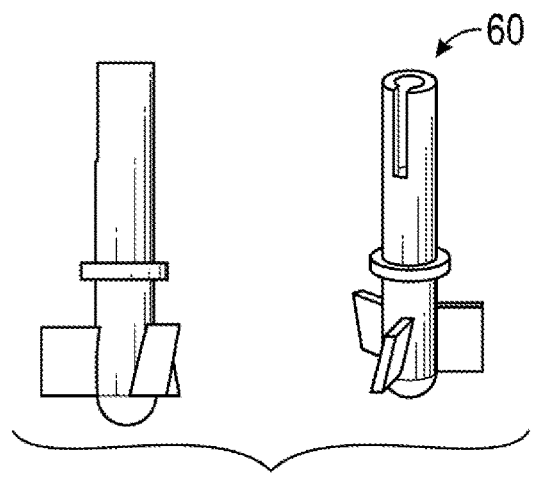
FIG. 2C is a series of views of a spin shaft of the cell culture system of FIG. 2A.
Figure 2D:
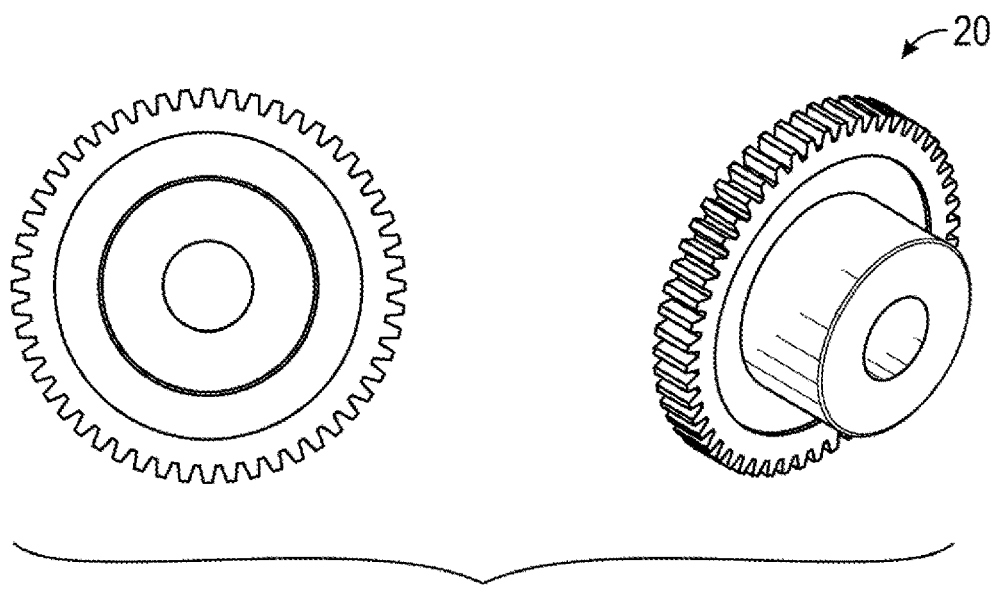
FIG. 2D is a series of views of a gear of the cell culture system of FIG. 2A.
Figure 2E:
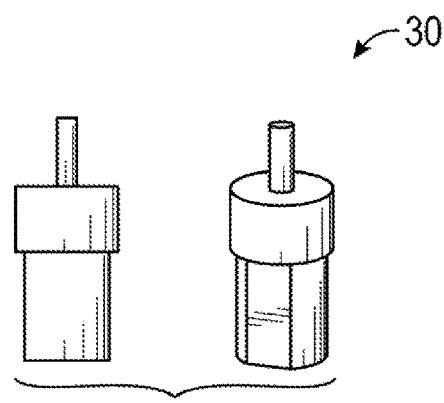
FIG. 2E is a series of views of a motor of the cell culture system of FIG. 2A.
Figure 2F:
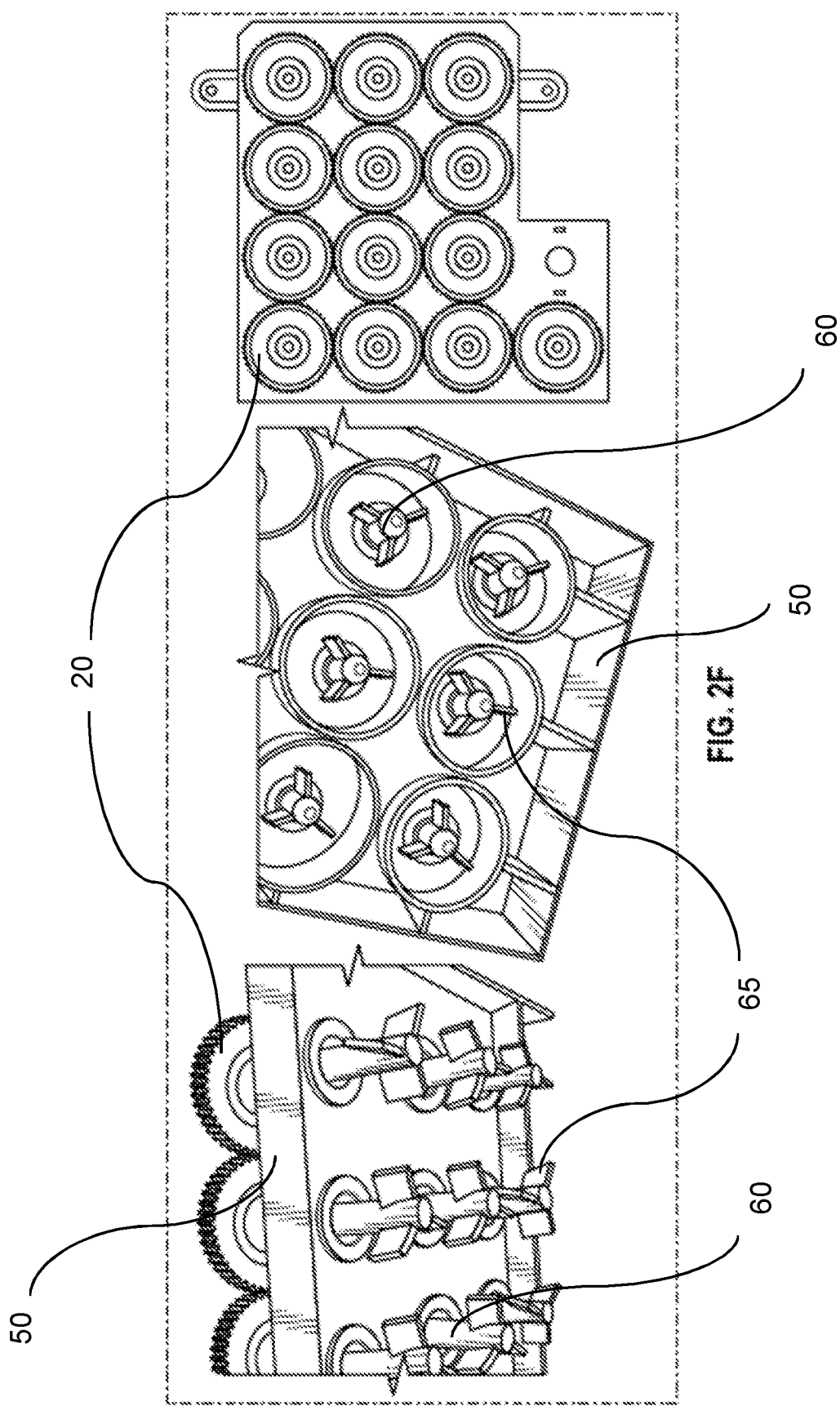
FIG. 2F is a series of views of components a cell culture system of FIG. 2A.
Figure 3A:
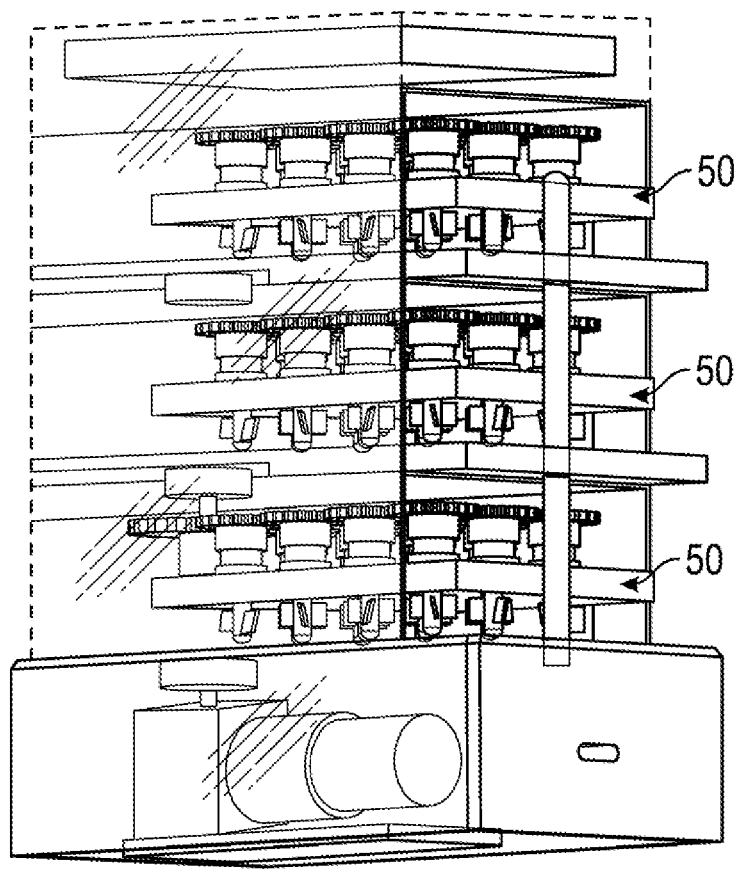
FIG. 3A is a schematic of a cell culture system and components thereof in a stackable embodiment of the invention.
Figure 3B:
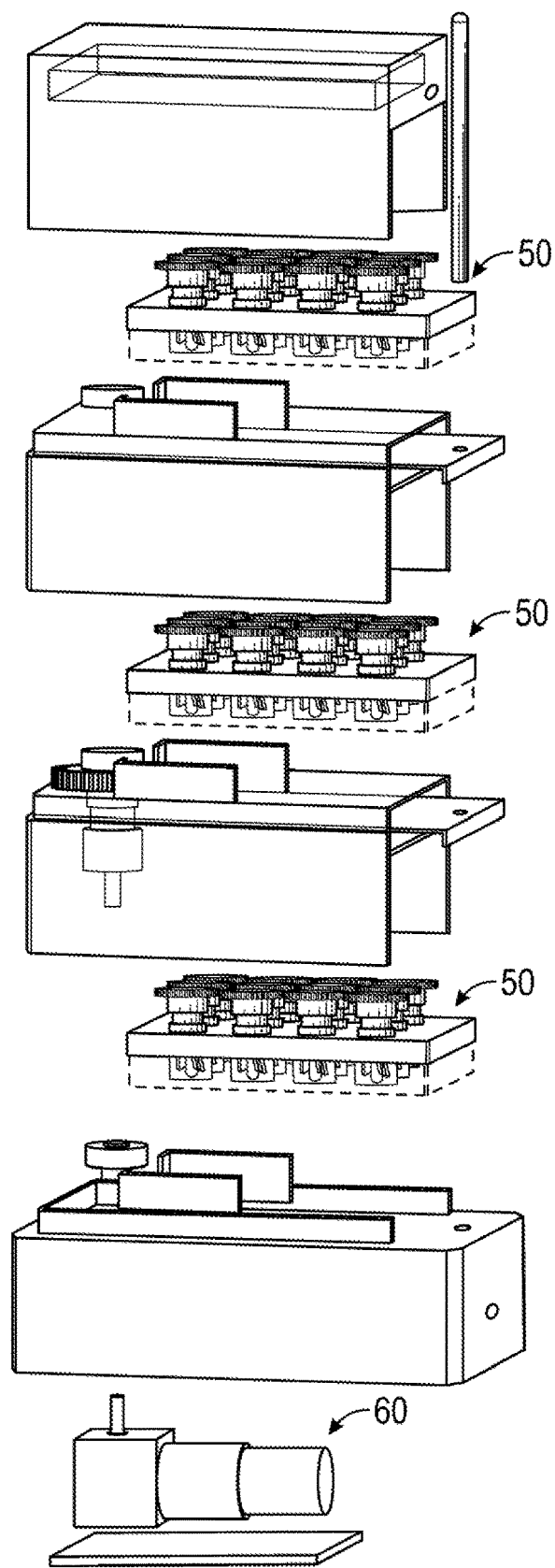
FIG. 3B is an expanded schematic of a cell culture system and components thereof of the cell culture system of FIG. 3A.
Figure 4:
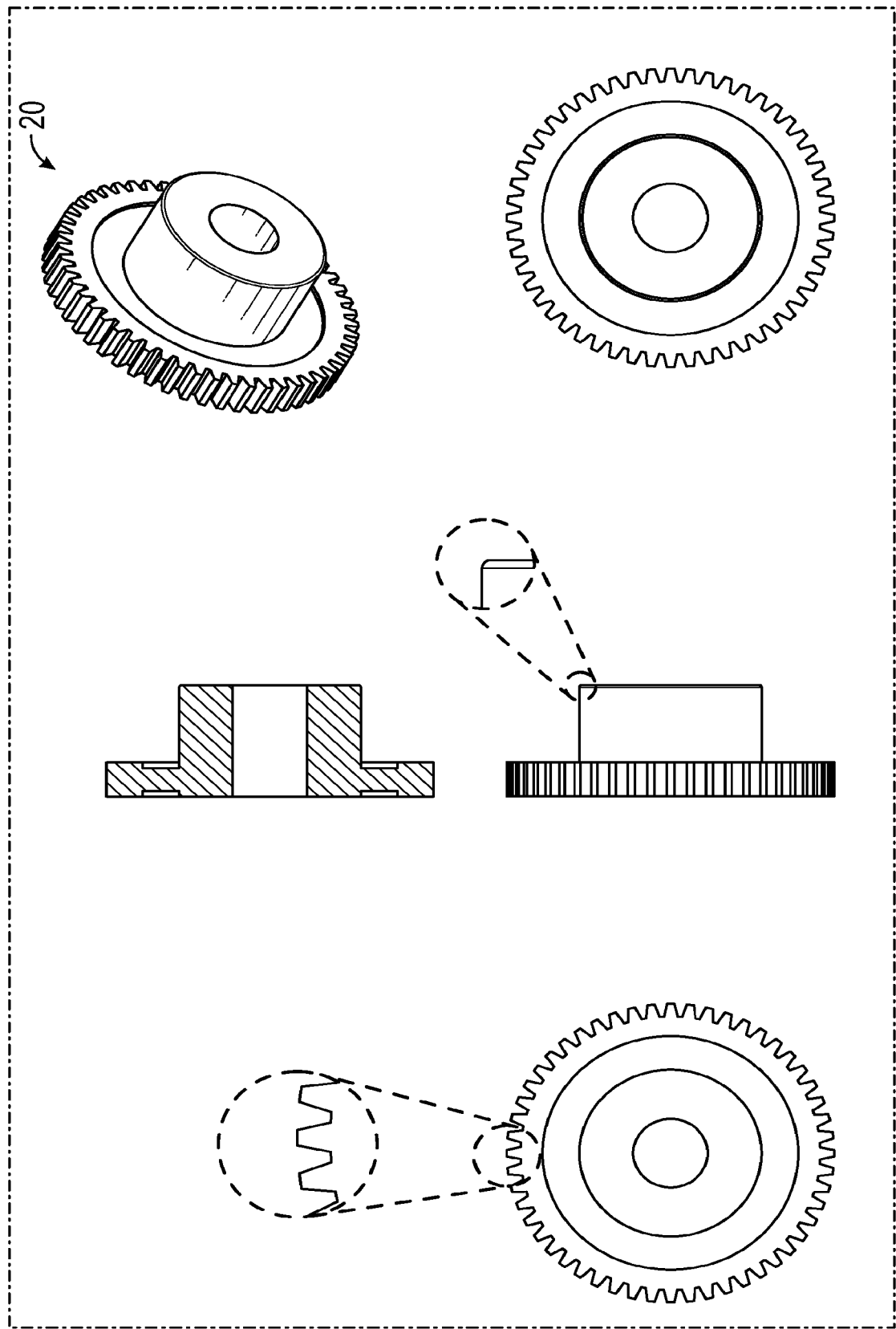
FIG. 4 is a series of schematics of a gear of the cell culture system of FIG. 1 or FIG. 3A.
Figure 5:
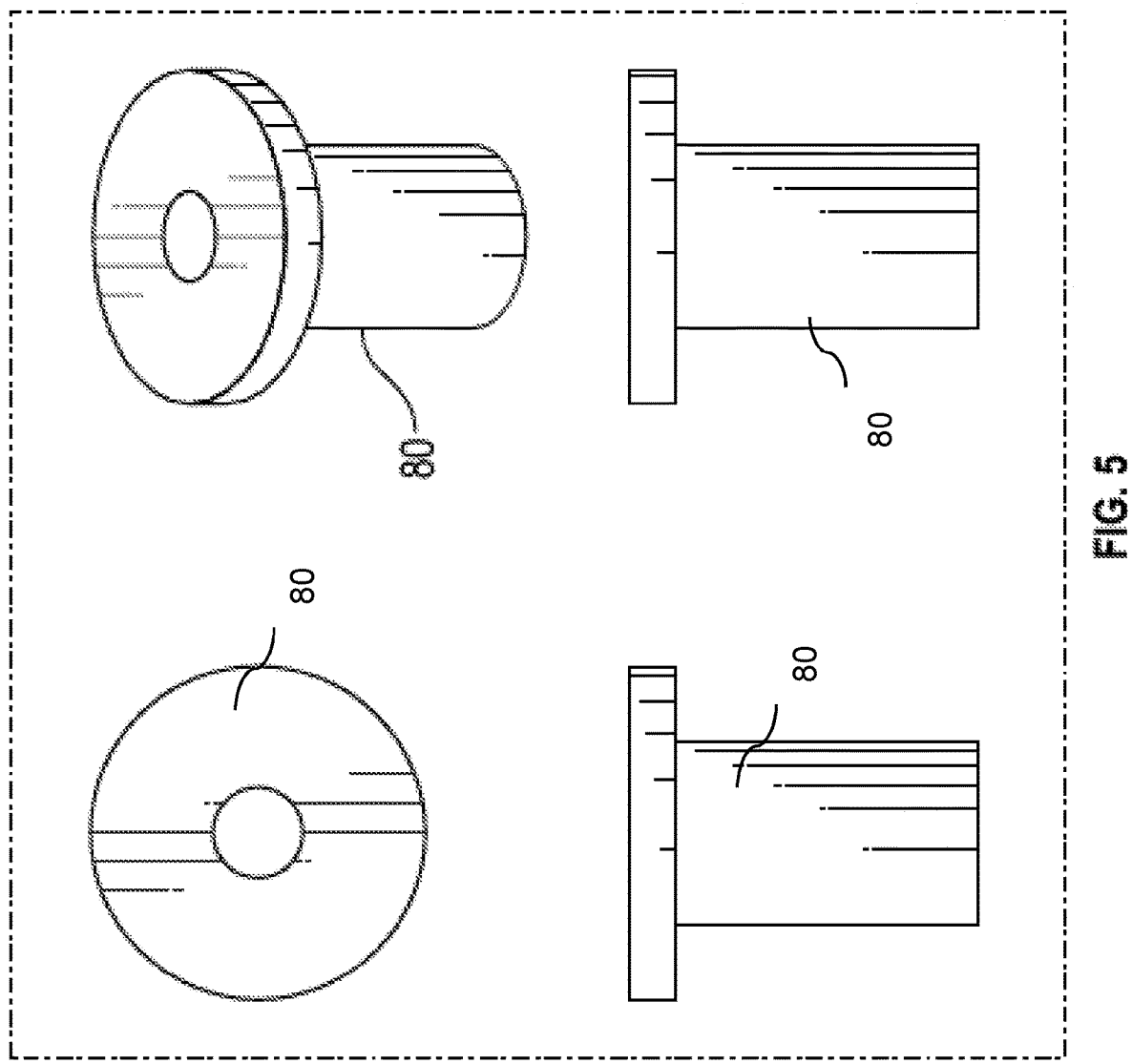
FIG. 5 is a series of schematics of an insert spacer of the cell culture system of FIG. 1 or FIG. 3A.
Figure 6:
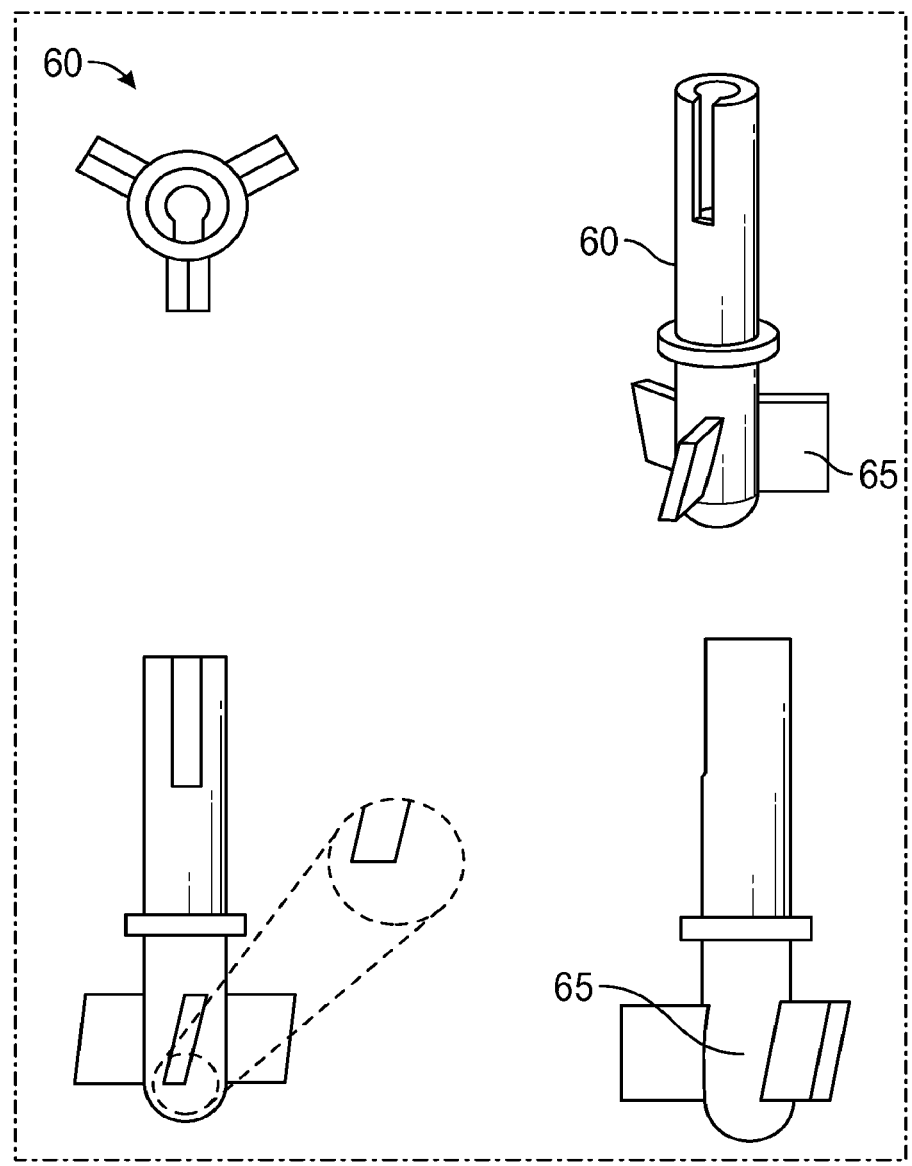
FIG. 6 is a series of schematics of a spinner shaft of the cell culture system of FIG. 1 or FIG. 3A having shaft paddles angled with respect to the longitudinal axis of the shaft.
Figure 7:
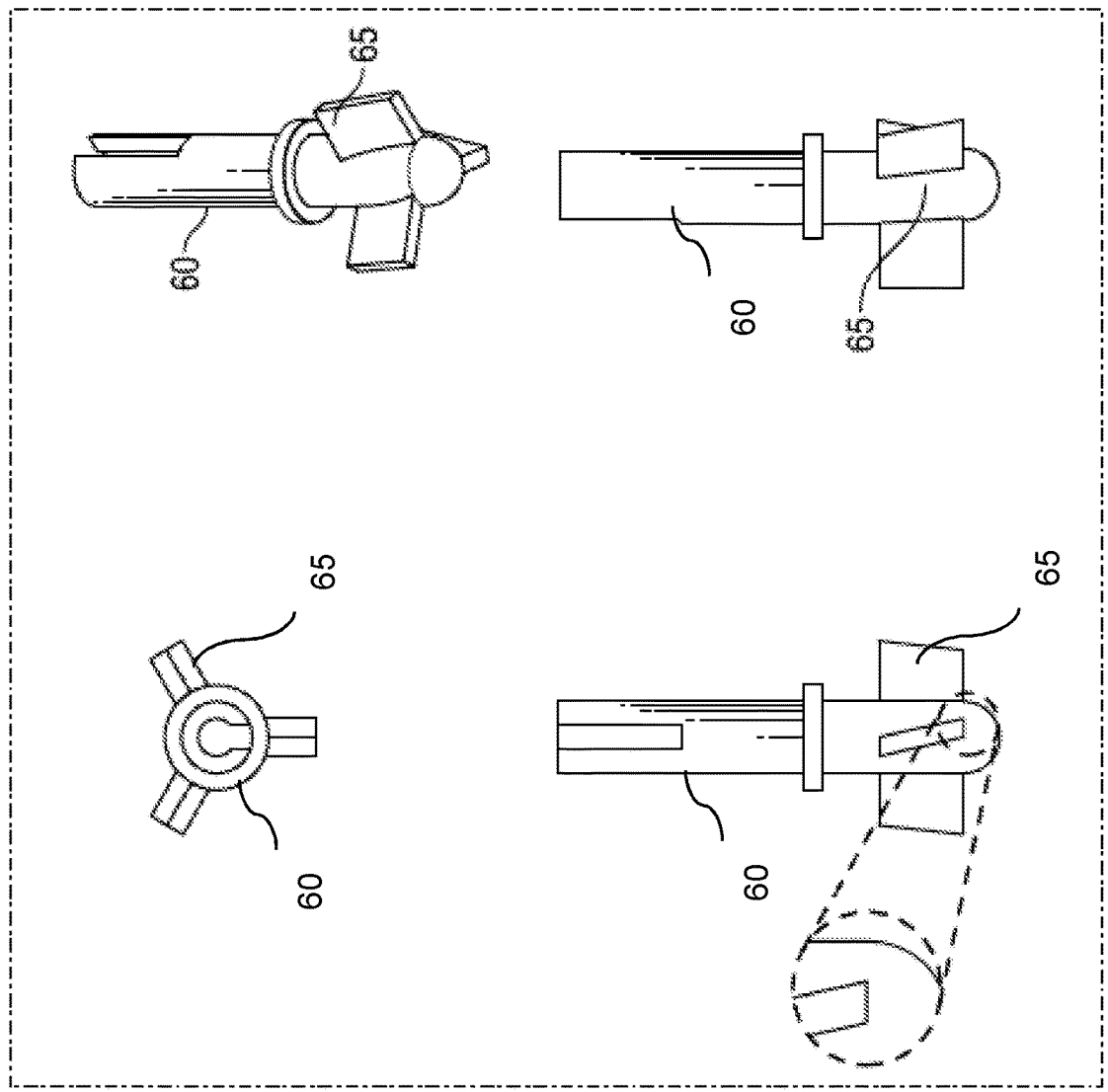
FIG. 7 is a series of schematics of a spinner shaft of the cell culture system of FIG. 1 or FIG. 3A having shaft paddles angled with respect to the longitudinal axis of the shaft.
Figure 8:
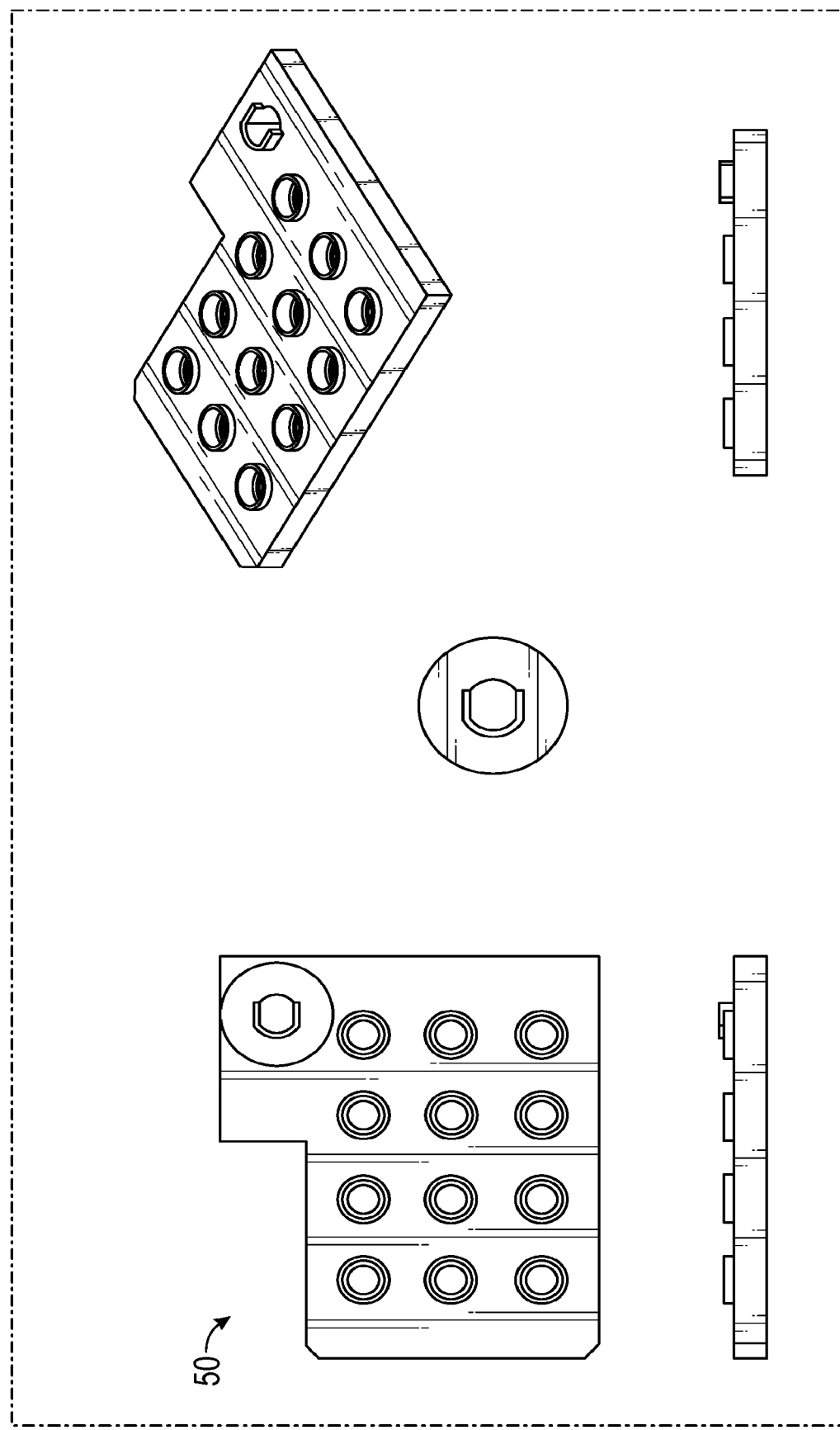
FIG. 8 is a series of schematics of the plate cover of the cell culture system of FIG. 1 or FIG. 3A.
Figure 9:
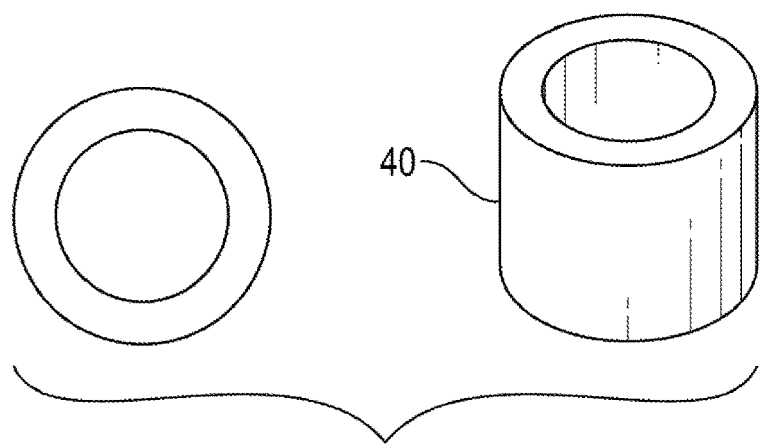
FIG. 9 is a series of schematics of a sleeve bearing of the cell culture system of FIG. 1 or FIG. 3A.
Figure 10:
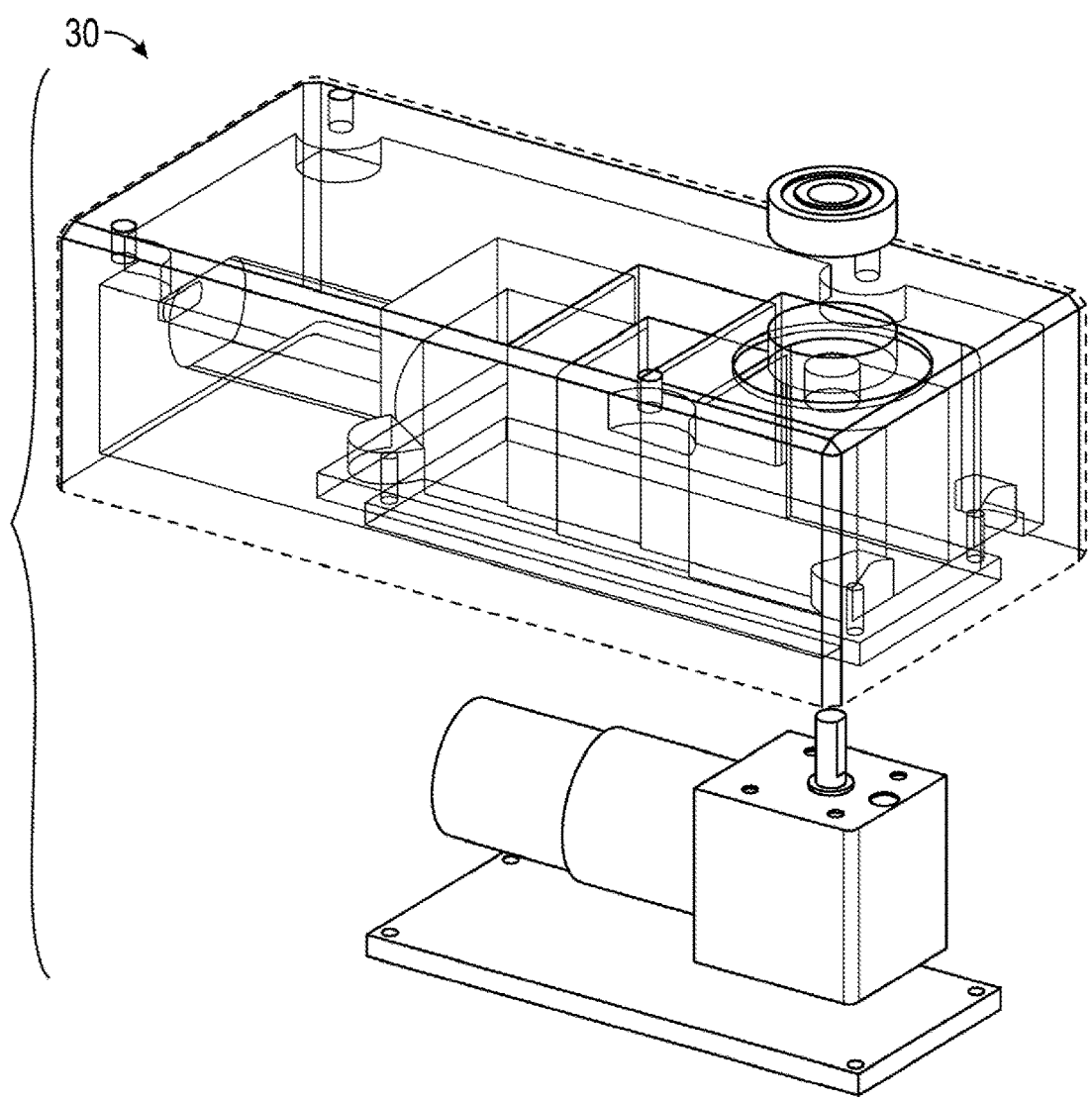
FIG. 10 is an expanded schematic of a motor and housing for use with a cell culture system in an embodiment of the invention.

As such, in one aspect, the present invention provides a cell culture system for culturing cells. With reference to FIGS. 1-11, the system 10 includes multiwell culture plate which has a base substrate 70 having a plurality of culture wells. Spinner shafts 60 are associated with each culture well, each shaft being configured to mix media present in each culture well and having a gear 20 adapted to operably associate with a gear 20 on a shaft associated with an adjacent culture well. The system further includes a motor 30 having a drive shaft in operable communication with the shaft gears 20, wherein rotation of the drive shaft causes rotation of each shaft 60 and mixing of the media in each culture well. In embodiments, the each shaft 60 is disposed in a cover plate 50 overlying the base substrate 70. The cell culture system may further include multiple multiwell culture plates, the plates being stackable and having shafts driven by a single motor as shown in the embodiment of FIG. 3.

In another aspect, the invention provides a method of cell culture. The method includes providing a cell culture system of the invention, and culturing a cell in a culture well in culture media under conditions suitable for cell culture, wherein the conditions comprise mixing of the cell culture via actuation of the motor, thereby culturing the cell.

Spin bioreactors has been used for 3D cell culture and generation of organ-like tissues (organoids). The circular flow provides better mixing of oxygen from the air into culture media and facilitates diffusion of oxygen and nutrients into cultured tissues. It enables non-attaching suspension culture in 3D, a condition that better recapitulate in vivo environments than traditional two-dimensional (2D) culture. In addition, the shear stress generated from the fluid flow is a mechanical cue to regulate cell growth and differentiation. Specifically, spinning culture has been shown to promote formation of continuous cerebral tissues derived from human stem cells.

However, current spin bioreactor products available on the market, for example, are not ideal for efficient organoid culture. Proportional reduction of current spinning bioreactor into smaller size does not provide the same fluid dynamics for efficient organoid culture.

The present invention provides a plate cover 50 fitting the dimensions of a base culture plate 70, such as a 6, 8, 9, 10, 12, 14, 15, 16, 18, 20, 21 or 24 well plate, and allowing simultaneous spinning in all the wells. Similar to the standard plate cover, while ensuring gas exchange from the side, SpinΩ's plate cover design contains no direct vertical opening to the outside and prevents contaminants from falling into wells.

Below the plate cover 50, the spin is generated by one or more paddles or fins 65 attached on each shaft 60. As the shaft spins, the paddles generate a circular laminar flow in the culture media, allowing cultured tissue to spin in suspension. The paddles are slightly tilted and create a lift as they rotate. Above the cover, the spin shafts are attached to a set of interconnecting gears 20 (thirteen gears shown in the embodiment of FIG. 1), driven by a single electric motor 30 to rotate in synchrony. A small, low-speed, high-torque DC gear motor is used to drive the rotation. The motor is sealed to elongate its operation lifespan within the high humidity inside incubator. The motor mount can be easily detached from the rest of the plate for sterilization by autoclave.

The plate and spin shafts can be manufactured by any conventional method, such as 3D printing using Ultem, or polyetherimide. Ultem has excellent heat resistance, capable of withstanding high pressure and temperature under autoclave. It also has superior mechanical strength comparing to most plastic materials. The spin shafts are supported by Teflon sleeve bearings, which offers minimal friction and the debris from wear is generally considered bio-inert.

The most significant advantage of SpinΩ over current products is that SpinΩ is miniaturized. SpinΩ is much smaller in size and its rectangular design is compact and takes space more efficiently. SpinΩ does not require dedicated incubator space, as it is self-driven and the setup requires no external equipment. Moreover, SpinΩ requires as little as 2 mL of media to support tissues growth, dramatically reducing the cost for maintaining tissue culture. This feature allows supplementing drugs and growth factors to media, which is unaffordable to many laboratories when using the bulky flask systems. In addition, SpinΩ's multi-well system enables researchers to conduct experiments more efficiently and systematically. It can be used to run parallel experiments under the same physical conditions, opening great potentials for applications in drug screening and toxicity testing.

In addition, the SpinΩ allows the tissue organoids to grow uniformly in complete 3D suspension. This feature allows the organoids to undergo their patterning free of interaction with the substrate below, whose contact can create friction that can shear the organoids and can affect the development of the organoids.

Advantages of the culture system described herein include the following.

Generate flow and lift: the key function of SpinΩ is provided by the spin shafts with fins on the side. The spin generates circular laminar flow within the wells. The fins are slightly tilted to generate a lifting force to ensure tissue culture constantly in suspension.

The speed of the spin shaft is tunable from 30-125 RPM, to ensure full suspension and flow of human iPSC-derived brain organoids from 200 micrometers to 3 millimeters in diameter.

High-throughput from multi-well system: SpinΩ uses interconnected set of gears to generate simultaneous spinning in multiple tissue culture wells driven by a single electric motor.

Modular design: Multiple plates can be stackable up to the limit of the incubator chamber or be used as a standalone single plate.

Miniaturization: SpinΩ takes minimal incubator space and consumes as little as 2 mL of culture media in each well, significantly reducing the space required and the media cost to maintain long-term culture.

Sterility: SpinΩ is made of autoclavable materials and can be easily sterilized. It does not contain vertical opening to outside, thus minimizing chance of contamination.

Biocompatibility: The parts in SpinΩ that contacts the cell culture is made of bio-inert plastics that provokes no cytotoxicity effects.

Self-driven: SpinΩ is driven by a small DC motor and does not require additional equipment to operate. The motor can be powered a small 9V battery or other power supply.

Compatible with standard multi-well plates: The current prototypes of SpinΩ are based on standard 6-well and 12-well plates in dimensions.

Co-culture of attaching and suspension cell types: The bottom plate can be used to culture attaching cell types (e.g., astrocyte, fibroblasts, etc.) while the 3D space is for suspension culture.

Components of the culture system are illustrated in FIGS. 1-11.

As used herein, "substances" include "culture media," "culture substances," "test substances," "agents" or "molecules" the names of which are used interchangeably herein, and are defined as a collection of covalently attached atoms having a molecular weight of less than 2 million Dalton and that have a finite (more than 0) solubility. This includes associated or aggregated molecules such as, for example, protein complexes or drug-receptor pairs.

Substances may at times be referred to as culturing substances or media and may include a variety of various molecules known in the art to be useful for, associated with, or assayed via cell culture. Substances may at times be referred to as molecules and may be nutrients, cellular waste products, toxic compounds, signaling molecules, growth factors, biomolecules, proteins, gases, such as oxygen, nitrogen, carbon dioxide, naturally occurring chemicals or compounds, environmental or industrial chemicals, drugs, pharmaceutical agents, sugars, such as glucose, and any combination thereof. Substances may at times be referred to as test substances may include a variety of various molecules known in the art to be useful for, associated with, or assayed via cell culture.

As discussed herein, the system of the present invention may be used with a variety of cell types and sizes. Further, the cells may be cultured in fluid culture medium, for example an appropriate nutrient medium and incubation conditions that supports growth of cells.

In one embodiment a system of the present invention is at a uniform temperature during culture. In embodiments of a system of the present invention, a convective flow is introduced to eliminate or reduce one or more gradients for some period of time. Convective flow can for example be introduced by mechanical agitation, fluidic devices, and thermal gradients.

In another aspect, the present invention provides a method of generating an organoid or tissue utilizing the culture system of the invention. The method includes a) providing one or more cells of a type appropriate for a specific tissue type; b) culturing the cells using the system described herein; and c) harvesting the resultant organoid or tissue, thereby generating a tissue. In various embodiments, the organoid or tissue may be a one, two or three-dimensional tissue, and incorporate one, or a variety of specialized cell types.

In various embodiments, cells may be cultured in suspension, or alternatively, cells may be seeded onto a surface and cultured in one or more organized layers. In this manner, it is possible of generating organoids which are capable of mimicking characteristics of functional organs, such as brain.

Virtually any type of cell may be used for culturing in the device depending on the tissue or organ to be mimicked. For example, by way of illustration and in no way limiting, such cell types include epithelial, endothelial, smooth-muscle, neural, cardiac, and immune cells. An illustrative list of eukaryotic cell types that can be used includes stem cells; pluripotent stem cells; primary cells; fibroblasts; motile cells, ciliated cells; cancer cells including cervix, ovary, colorectal breast, prostate, bladder, pancreas, kidney, lung, salivary gland, testis, cecum, liver, colon, mammary gland, vulva, stomach, pleura, bladder, brain, bone, bone marrow, lymph, eye, connective tissue, pituitary gland, muscle, heart, spleen, skin, uterus, endometrium cells, epithelial cells; endothelial cells; blood cells; neural cells; secretory cells including adrenal gland cells; contractile cells including smooth muscle cells and skeletal muscle cells; hepatocytes; adipocytes; lymphocytes; macrophages; T-cells; B-cells; dendritic cells; neurons; chrondrocytes, and stem cells including embryonic, fetal, amniotic, adult and induced pluripotent stem cells. Examples of some cell types listed above include Swiss 3T3, NIH 3T3, MDA-MB-231, MCF-7, HEPG2, CHO, CACO-2, MDCK, B16-F1, B16-F10, HUVEC, PC-12, WI-38, HDF, and SW-13 cell lines.

The cells may be cultured within the device in gas and/or liquid fluid culture medium. Many commercially available media such as Dulbecco's Modified Eagles Medium (DMEM), RPMI 1640, Fisher's, Iscove's, and McCoy's, may be suitable for supporting the growth of the cell cultures. The medium may be supplemented with additional substances such as salts, carbon sources, amino acids, serum and serum components, vitamins, minerals, reducing agents, buffering agents, lipids, nucleosides, antibiotics, attachment factors, and growth factors. Formulations for different types of culture media are described in various reference works available to the skilled artisan (e.g., Methods for Preparation of Media, Supplements and Substrates for Serum Free Animal Cell Cultures, Alan R. Liss, New York (1984); Tissue Culture: Laboratory Procedures, John Wiley & Sons, Chichester, England (1996); Culture of Animal Cells, A Manual of Basic Techniques, 4th Ed., Wiley-Liss (2000)).

In one embodiment, the system is utilized to generate brain associate organoids, e.g., forebrain-specific organoids as discussed in the Examples. Such organoids may serve as biological models for screening agents, as well as therapeutic tissue for treating diseases or disorders in a subject, for example, regenerative medicine applications.

The system of the present invention may also incorporate other physical, chemical, or electronic components necessary or desirable for a given objective of the cell culture. For example, it may be connected to other apparatuses and/or instruments for proper operation of the culturing processes, as would be apparent to and understood by a person skilled in the art of bioprocess engineering. In one embodiment, the system may further include a fluid or exchange apparatus to exchange or modify the culture medium in the bulk.

In another embodiment, a biological agent may be contacted with the cultured cells. Such an agent may include one or more ligands, such as drugs or drug candidates, natural compounds, toxins, smoke, allergens, molds, pollen, nanoparticles, mineral dust, nucleic acids, viruses, bacteria, microbes, cells, hormones, growth factors, and cytokines. In one embodiment, the cells are infected with a virus, such as a flavivirus including Zika or Dengue.

To promote cellular attachment and growth of seeded cells, components of the device, may further be coated with one or more cellular attachment molecules. Such molecules include collagen, fibronectin, laminin, poly-D-lysine, poly-L-ornithine, proteoglycan, vitronectin, polysaccharide and combinations thereof.

In various embodiments the sample well may be formed from a material which is compatible with cells; e.g., biocompatible. Suitable materials can include, glass, ceramics, metals, plastics, polymers including, but not limited to polystyrene, polycarbonate, polypropylene or polymeric thin films.

In various embodiments one or more surfaces of the device may be coated with a suitable culture substrate the promotes cell adhesion. Likewise, the porous membrane may be coated. In embodiments, the substrate can be formed from, but is not limited to, one or more of collagen, laminin, fibronectin, Matrigel™, agarose, or agar. In some embodiments, the substrate is formed from one or more of collagen, including, for example, type I collagen and/or type IV collagen, and fibronectin. Different concentrations of the substrate material may be utilized to alter the substrate properties. In various embodiments the substrate includes one or more of a polypeptide, entactin, glycoprotein, collagen, fibronectin, laminin, poly-D-lysine, poly-L-ornithine, proteoglycan, vitronectin, polysaccharide, hydrogel, and combinations thereof.

The wells of the device may also include three-dimensional culture surfaces. Such surfaces may have interstitial spaces for attachment and growth of cells into a three dimensional tissue. The openings and/or interstitial spaces of the framework in some embodiments are of an appropriate size to allow the cells to stretch across the openings or spaces. Maintaining actively growing cells stretched across the framework appears to enhance production of the repertoire of growth factors responsible for the activities described herein. Any shape or structure that allows the cells to continue to replicate and grow for lengthy time periods may function to elaborate the cellular factors in accordance with the methods herein.

In some embodiments, the three dimensional culture surface is formed from polymers or threads that are braided, woven, knitted or otherwise arranged to form a framework, such as a mesh or fabric. The materials may also be formed by casting of the material or fabrication into a foam, matrix, or sponge-like scaffold. In other aspects, the three dimensional framework is in the form of matted fibers made by pressing polymers or other fibers together to generate a material with interstitial spaces. The three dimensional framework may take any form or geometry for the growth of cells in culture.

A number of different materials may be used to form a culture substrate of the device. These materials include non-polymeric and polymeric materials. Polymers, when used, may be any type of polymer, such as homopolymers, random polymers, copolymers, block polymers, coblock polymers (e.g., di, tri, etc.), linear or branched polymers, and crosslinked or non-crosslinked polymers. Non-limiting examples of materials for use as scaffolds or frameworks include, among others, glass fibers, polyethylenes, polypropylenes, polyamides (e.g., nylon), polyesters (e.g., dacron), polystyrenes, polyacrylates, polyvinyl compounds (e.g., polyvinylchloride; PVC), polycarbonates, polytetrafluorethylenes (PTFE; TEFLON), thermanox (TPX), nitrocellulose, polysaccharides (e.g., celluloses, chitosan, agarose), polypeptides (e.g., silk, gelatin, collagen), polyglycolic acid (PGA), and dextran.

The cells may be cultured for any duration of time appropriate for forming a particular tissue structure. In embodiments, cells are culture from about 2 to 100 days, for example, between about 3 to 80 days, 4 to 21 days or 5 to 14 days.

During the incubation period, the cultured cells grow and expand to form an organoid. The growing cells may produce a myriad of growth factors, regulatory factors and proteins, some of which are secreted in the surrounding media, and others that are introduced into the culture medium as differentiation factors. Growth and regulatory factors can be added to the culture during incubation to induce differentiation of the cells to the desired cell type.

Culture conditions are typically under appropriate conditions of pH, temperature, and gas (e.g., $O_2$, $CO_2$, etc.) to maintain a growth condition suitable for the particular tissue being mimicked. In some embodiments, the cell culture can be grown in monolayers. In addition, the culture may be "fed" periodically to remove the spent media, depopulate released cells, and add new nutrient source.

In order to determine the amount of a particular type of a cell in a cell culture or cell population, a method of distinguishing this cell type from the other cells in the culture or in the population may be used. Accordingly, in one embodiment, the methods further relate to cell markers whose presence, absence and/or relative expression levels are specific for specific cell types. As used herein, "expression" refers to the production of a material or substance as well as the level or amount of production of a material or substance.

Thus, determining the expression of a specific marker refers to detecting either the relative or absolute amount of the marker that is expressed or simply detecting the presence or absence of the marker. As used herein, "marker" refers to any molecule that can be observed or detected. For example, a marker can include, but is not limited to, a nucleic acid, such as a transcript of a specific gene, a polypeptide product of a gene, a non-gene product polypeptide, a glycoprotein, a carbohydrate, a glycolipid, a lipid, a lipoprotein or a small molecule.

One or more of the culture surfaces, for example the surfaces of the culture wells, may be derivatized or coated before or during culture with extracellular matrix molecules, adhesion ligands, growth factors, receptors, and the like as discussed herein. The use and benefits of coating the surfaces of a culture chamber is known to a person skilled in the art.

The culture surfaces of the device may be made reactive so that other molecules may be covalently linked. The surface can be made reactive in various ways known to those skilled in the art, for example by treatment with such molecules as aminopropyltrimethoxysilane (APTS), which presents amine groups on the surface. Thin layers or bulk materials may be linked to the surface. Bulk materials include gels made from protein, polyacrylamide, or other materials. Such gels may be formed in molds made with standard microfabrication techniques. The gels may be placed on the surface and covalently bound into place by reaction with the activated surfaces. For example, collagens or fibronectin may be used.

The surfaces may be derivatized with binding proteins that a target cell type is normally exposed to in a natural environment, such as claudin and occludin (for tight junctions), cadherins (for actin-linked, adherens junctions), co unexins (for gap junctions), and selectins (for selectin-lectin interactions)). Thin layers of proteins may be patterned on the surfaces, for example by treatment of the APTS-treated surface with glutaraldehyde, or with the photoactivatable cross-linker 4-benzoylbenzoic acid succinimidyl ester, or by using other techniques known to those skilled in the art. The proteins may be of any type. The proteins may be patterned in concentration gradients on surfaces by methods known to those skilled in the art.

A control system such as a computer or other automation devices (not shown in the figures) may be used to monitor and control the operation of the device, and to analyze obtained data. The culturing environment may be adjusted dynamically based on the information gathered in real time. Media flow and metabolite concentrations can be monitored and controlled. For example, sensors may be connected to the control system using electrodes and may be used to simultaneously measure the concentration of oxygen and the pH value in the culture spaces. Further, with multiple sensors, the gradient of a given material in the chamber can be measured. Feedback information may include values of pH, glucose and oxygen concentrations, temperature, osmolarity, shear forces, and the like.

Electrical conductors may be embedded in the device for connecting sensor and pump electrodes to external electronics and power sources. The conductors may be deposited using standard microelectronics fabrication techniques. For example, the conductors may have a thickness on the order of nanometers. A conductor may run along the surface of a substrate or through the substrate. Conductors may also be covered with inert coatings with non-conducting materials such as aluminum oxide.

As mentioned earlier, computers and computer programs can be used to control the culturing and monitoring of cells and to analyze obtained data. Microprocessors can be incorporated into the device or in a separate centralized unit. The computer system can record the measurements from the sensors, analyze the data, and control the culture parameters accordingly. The culture chamber and accessory devices may be monitored and controlled by one or multiple processors and software programs.

In another aspect, the present invention provides a kit for performing cell culture. In various embodiments, the kit includes a culture system of the present invention. The kit may optionally further include cells, culture media, reagents for detecting a cellular or biological activity, instructions for using the kit in accordance with any of the described methods, and tools for customizing the culture system. The kit may be configured in a multiwell format for high throughput automation.

The following examples are provided to further illustrate the advantages and features of the present invention, but are not intended to limit the scope of the invention. While they are typical of those that might be used, other procedures, methodologies, or techniques known to those skilled in the art may alternatively be used.

Example 1

Generation of Organoids

This example illustrates culture of cells using the culture system according to FIGS. 1-11 to generate organoids.

The culture system allows tissue organoids to grow uniformly in complete 3D suspension. This feature allows the organoids to undergo their patterning free of interaction with the substrate below, avoiding contact friction that can shear the organoids and can affect the development of the organoids.

The culture system was successfully used to develop a highly-reliable protocol to generate human induced pluripotent stem cell-derived organoids patterned for cerebral cortex, midbrain, hypothalamus and hippocampus.

Different brain regions were generated using the 12-well culture system (data not shown). After 30-85 days of differentiation, iPSCs differentiated into 3D aggregates with characteristic features of different brain regions.

Culture conditions were systemically tested to optimize protocols. Additionally, screening was performed to test the effects of Bisphenol A (BPA) on neurogenesis in the organoid system.

Toxin screening was performed using the 12-well culture system. Images of the effect of different concentrations of BPA on human developing cerebral cortex organoids were taken (data not shown). Quantification of the proliferation rate of neuronal precursor cells in human organoids was performed showing a dose-dependent effect of BPA toxicity.

Example 2

Brain-Region-Specific Organoids Using Mini-Bioreactors for Modeling ZIKV Exposure Cerebral organoids, three-dimensional cultures that model organogenesis, provide a new platform to investigate human brain development. High cost, variability, and tissue heterogeneity limit their broad applications. Here, we developed a miniaturized spinning bioreactor (SpinΩ as shown in FIGS. 1-11) to generate forebrain-specific organoids from human iPSCs. These organoids recapitulate key features of human cortical development, including progenitor zone organization, neurogenesis, gene expression, and, notably, a distinct human-specific outer radial glia cell layer. We also developed protocols for midbrain and hypothalamic organoids. Finally, we employed the forebrain organoid platform to model Zika virus (ZIKV) exposure. Quantitative analyses revealed preferential, productive infection of neural progenitors with either African or Asian ZIKV strains. ZIKV infection leads to increased cell death and reduced proliferation, resulting in decreased neuronal cell-layer volume resembling microcephaly. Together, our brain-region-specific organoids and SpinΩ provide an accessible and versatile platform for modeling human brain development and disease and for compound testing, including potential ZIKV antiviral drugs.

Human-induced pluripotent stem cells (iPSCs) can generate virtually any cell type in the body to model human development and disease, screen for therapeutic drugs, and develop cell-replacement therapies. Traditional monolayer cultures allow for external control of targeted differentiation of human iPSCs to produce more uniform cell populations; however, these cultures lack 3D cell assembly properties that define endogenous biological systems. Structures resembling whole developing organs, named organoids, have recently been generated via 3D cultures and include intestinal, kidney, retinal, and cerebral organoids. Organoid technology evolved from embryoid body cultures, which are 3D aggregates of stem cells that self-organize to develop disparate tissues in vitro, similar to teratoma formation in vivo. Organoids provide a unique opportunity to model human organogenesis, which is not accessible to experimentation. An immediate application of organoid technology would be to address the current global public health emergency concerning a suspected link between Zika virus (ZIKV) and microcephaly, a neurodevelopmental disorder, by modeling human brain development.

One recent advance in cerebral organoid technology was the adoption of a spinning bioreactor to facilitate nutrient and oxygen absorption, which enables formation of longer neuroepithelium-like zones and supports growth of large, complex organoids that more closely resemble the developing human brain than had been achieved by previous approaches. Derived from an early NASA-designed rotating wall vessel bioreactor to simulate microgravity, this technology potentially offers two additional benefits: (1) low fluid shear stress to promote cell-cell interactions and induction of differentiation and (2) randomized gravitational vectors that affect intracellular signal transduction and gene expression.

Despite the promise of these pioneering organoid technologies, there are several major challenges. First, available spinning bioreactors require a large volume of medium and incubator space. With frequent media changes over several months of culturing, the system is cost prohibitive for most laboratories and precludes scalability, use of growth factors, or chemical screening. It also presents a roadblock for testing different conditions to optimize protocols. Second, the current cerebral organoid methodology ("intrinsic protocol") is based on cell self-assembly without external control, and thus each organoid is typically comprised of diverse cell types found in forebrain, hindbrain, and retina. Large sample-to-sample variability associated with current methods complicates quantitative analyses and limits applicability. Third, key features of human brain development have yet to be robustly recapitulated in cerebral organoids. For example, unlike rodents, the embryonic human cerebral cortex contains an abundant population of specialized outer radial glia cells (oRGCs) in the outer subventricular zone (oSVZ), the cellular population considered pivotal to the evolutionary increase in human cortex size and complexity. Current cerebral organoids contain only sparse progenitors that have morphological characteristics of oRGCs, and none have exhibited a well-developed oSVZ layer. Taken together, there is a critical need to develop an organoid platform with reduced cost, higher throughput, and increased reproducibility and one that better resembles critical aspects of human cortical development.

To address these challenges, we engineered a miniaturized spinning bioreactor using 3D design and printing technology and developed a protocol to generate forebrain-specific organoids from human iPSCs, which recapitulate human embryonic cortical development in a reproducible and quantifiable manner. We also developed protocols for midbrain and hypothalamic organoids. For proof-of-principle applications of our platform, we performed chemical compound testing and modeled ZIKV exposure. Our versatile, simple-to-use, cost-effective, and reproducible brain-region-specific organoid platform provides accessible and affordable technology to a broad scientific community for modeling human organogenesis and human disorders and for compound testing.

Results

A Miniaturized Spinning Bioreactor to Optimize Organoid Cultures

Figure 11:
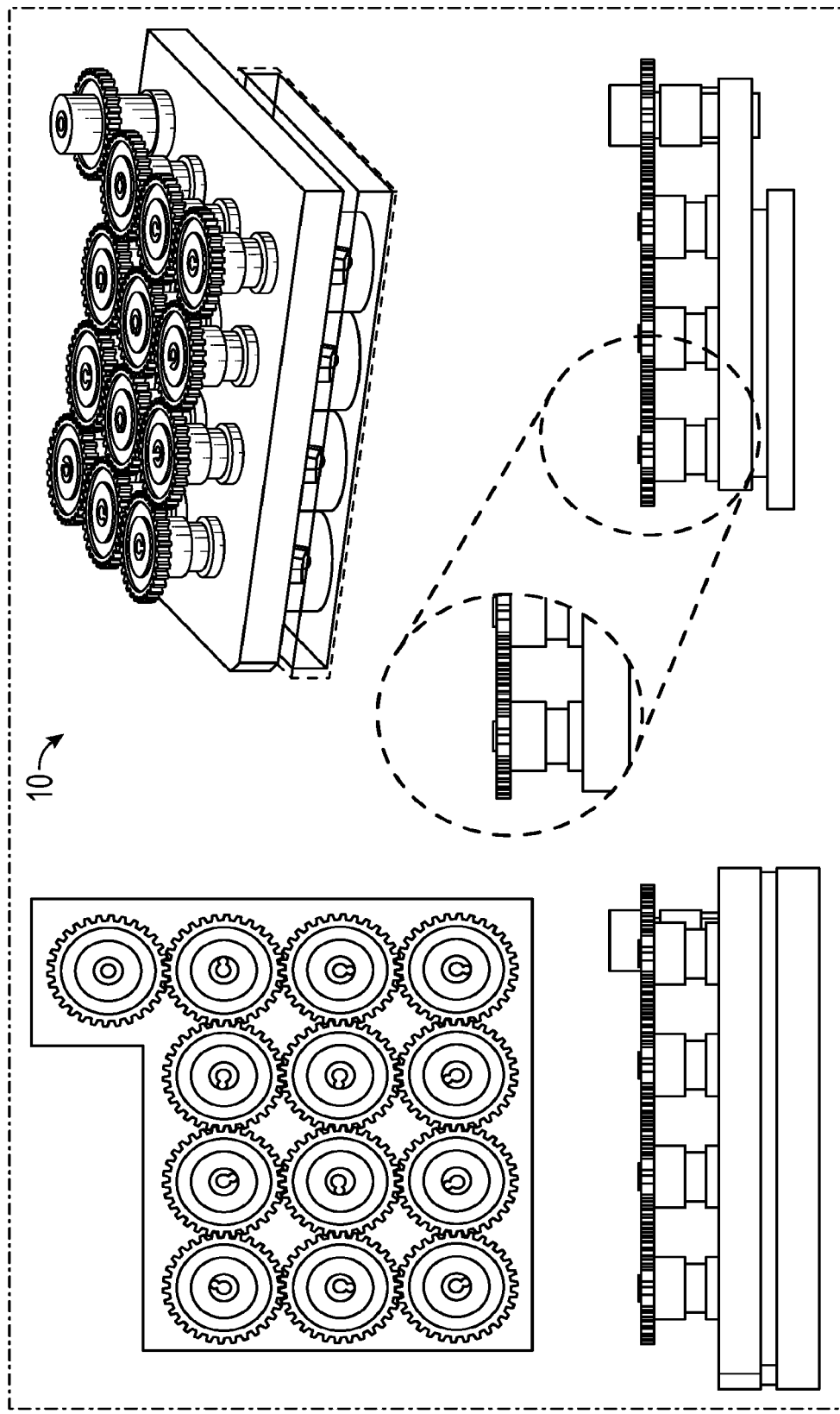
FIG. 11 is a series of images illustrating a plate cover assembly including spinner shafts and gears for use in a cell culture system in an embodiment of the invention.

To reduce the cost of generating organoids under different conditions, we attempted to miniaturize the large spinning flask. Nonlinear fluid dynamics precluded simply scaling down the system. Instead, we engineered a multi-well spinning device to fit a standard 12-well tissue culture plate. Above the cover, spinning shafts are attached to a set of 13 interconnecting gears, driven by a single electric motor (FIG. 11). We used computer-aided design software to design and 3D print each component. We assembled prototypes to optimize designs that sustain organoids of varying sizes in suspension under moderate spinning speed and prevent aggregation at the center of each well. After multiple rounds of systematic optimization of individual components, including number, shape, size, and angle of leafs and diameter, length, and shape of shafts, we arrived at SpinΩ, a miniaturized spinning bioreactor unit that requires as little as 2 ml of media per well, a 50-fold reduction in media consumption, and drastically reduced incubator space due to stackability of the SpinΩ system. We further designed a modular stackable version with insertable cassettes driven by one common motor (FIG. 2). The miniaturized spinning bioreactor permits comparisons of a large number of conditions in parallel for protocol optimization.

Figure 12:
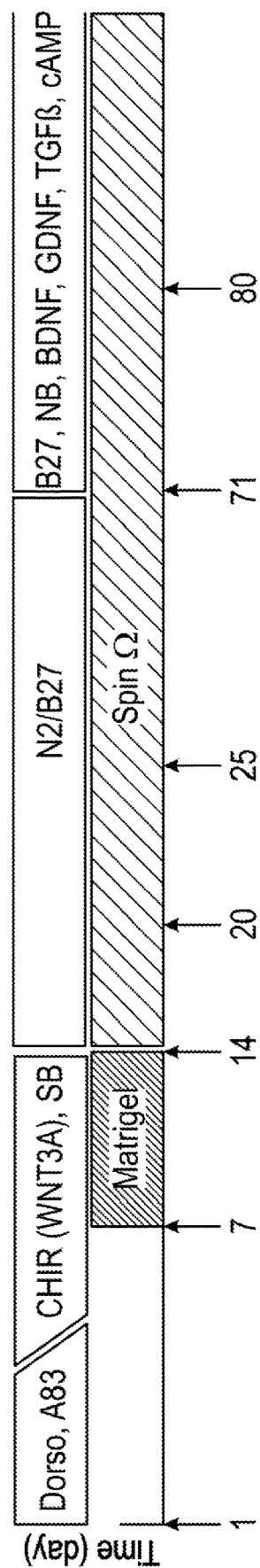
FIG. 12 is a schematic diagram of a forebrain organoid protocol utilizing the cell culture system.

To reduce tissue heterogeneity, we pre-patterned embryoid bodies to the fate of a specific brain region. We first treated human iPSCs with dual SMAD inhibitors (dorsomorphin and A-83) for 7 days and then embedded embryoid bodies in Matrigel for another 7 days, followed by Matrigel removal and spinning in SpinΩ (FIG. 12). Compared to the "intrinsic protocol," we could reliably generate organoids from multiple iPSC lines with reduced heterogeneity in organoid shape and size (data not shown). However, there was significant cell death within organoids, as shown by activated caspase-3 (CAS3) immune-staining (data not shown). We then tested combinations of different signaling molecules for various durations. We found that treatment with three factors, GSK-3b inhibitor CHIR99021, recombinant WNT3A protein, and SMAD inhibitor SB-431542, during the Matrigel stage drastically reduced the number of CAS3+ cells at day 14 (data not shown). Later, we determined that the WNT3A contribution was minimal, likely because WNT3A and CHIR99021 activate the same downstream signaling pathway (data not shown). At day 14, well-defined polarized neuroepithelium-like structures resembled neural tubes, with a nearly pure population of NESTIN+SOX2+ NPCs and expression of adherent junction markers (b-CATENIN and PKC1) and proliferation marker phosphohistone H3 (PH3) near the ventricular surface (data not shown). Notably, individual neuroepithelium-like structures were consistently much larger than those generated without treatment of these factors (data not shown). Upon spinning in SpinΩ, organoids developed into multi-layer stratified structures, composed of SOX2+NPCs, TBR2+ intermediate progenitor cells (IPCs), and CTIP2+ neurons (data not shown). With a small volume, it became affordable to supplement media with growth factors at later stages (data not shown).

In comparison, we maintained organoids in stationary cultures after day 14. At day 42, there was substantial cell death in the interior (data not shown). Ventricular structures were largely absent; instead, extensive neurogenesis without defined organization was observed (data not shown). We also cultured forebrain organoids using orbital shakers under a similar rotation speed as spinning in Spina. At day 42, organoids showed substantial cell death in the neuronal layer despite retaining defined ventricular structures (data not shown). These results suggest that spinning cultures enhance cell viability and promote maintenance of the stem cell niche, at least for forebrain organoids generated using our protocol. The miniaturized spinning bioreactor platform opens doors for cost-effective generation of organoids and provides accessible and affordable organoid technology to a broader scientific community.

Organoids with a Forebrain Identity and Increased Homogeneity

We next performed detailed characterizations of early stage forebrain organoids. At day 14, immunohistological analysis showed almost exclusive expression of forebrain-specific progenitor markers, including PAX6, OTX2, and FOXG1, with minimal expression of markers for other brain regions tested (data not shown). We obtained similar results with multiple iPSC lines and with different clones (data not shown). Consistent with previous findings, cerebral organoids generated in large spinning flasks using the "intrinsic protocol" exhibited diverse brain region identities with fewer than 50% of rosettes expressing PAX6 or OTX2 (data not shown).

We further assessed the temporal consistency of neuronal differentiation by quantifying the relative thickness of SOX2+ ventricular zone-like (VZ) layer and TUJ1+ neuronal layer between apical and basal surfaces at specific time points. At day 14, organoids generated using the "intrinsic protocol" exhibited varying degrees of neurogenesis with mixed cell types, whereas very few TUJ1+ neurons were detected in forebrain organoids (data not shown). As a result, our protocol produced organoids with nearly all cells organized in the VZ layer at this stage. By day 28, we observed a consistent ratio between SOX2+ progenitor layer and TUJ1+/CTIP2+ neuronal layer in forebrain organoids, compared to the large variability using the "intrinsic protocol" (data not shown).

The apparent homogeneity of forebrain organoids, small volume per condition, and multi-well format of SpinΩ comprise a platform that is amenable to chemical compound testing. As a proof of principle, we tested the effect of Bisphenol A (BPA), which is commonly found in household plastic products and is known to affect rodent neural development. Treatment of forebrain organoids from days 14 to 28 with BPA led to a dose-dependent decrease in the relative VZ thickness at day 28 (data not shown). With acute treatment of higher BPA concentrations for 24 hr and then pulse-labeling proliferating cells with EdU (data not shown), quantitative analysis showed decreased density of EdU+ or PH3+ NPCs (data not shown), indicating that reduced NPC proliferation contributes to decreased relative VZ thickness.

Multiple Progenitor Zones Recapitulating Human Embryonic Cortical Development

To characterize developmental dynamics, we systematically performed immunohistochemical analyses of day 28, 56, and 84 organoids. We observed well-defined VZ-like structures with packed SOX2+NPCs near the lumen at all three time points (data not shown). At day 28, a layer containing a mixture of TBR2+ IPCs and CTIP2+ neurons formed above the VZ, reminiscent of the preplate (PP) in human cortical development (data not shown). By day 56, distinct SVZ-like structures containing a mixture of SOX2+ NPCs, TBR2+ IPCs, and immature neurons formed above VZ, whereas cortical plate-like (CP) structures containing pure CTIP2+ neurons formed above VZ and SVZ (data not shown).

One hallmark of embryonic human cerebral cortex is the prominence of specialized oRGCs in the oSVZ layer. Similar to the developing human cortex, a thin gap appeared to separate the expanded SVZ in day 84 organoids into an inner SVZ-like (iSVZ) region that contained densely packed TBR2+ IPCs and an oSVZ-like region (data not shown). Recent studies have identified markers preferentially expressed by oRGCs in the developing human cortex, including HOPX, FAM107A, and PTPRZ1. Using antibodies that we validated with gestational week 22 (GW22) human tissue (data not shown), we found a large number of SOX2+HOPX+ oRGCs in day 84 organoids (data not shown). Previous cerebral organoid protocols generated only sparse NPCs with apparent oRGC characteristics, which did not organize into a progenitor layer outside of VZ. In contrast, our forebrain organoids exhibited a distinct SOX2+HOPX+ oSVZ-like layer separated from the SOX2+ HOPX− VZ layer (data not shown). We sometimes observed HOPX+ radially oriented basal processes from these oRGCs with pial contact but lacking an apical process, a hallmark of human oRGCs (data not shown). Two other oRGC markers, FAM107A and PTPRZ1, were also specifically expressed in oSVZ (data not shown). Many oSVZ SOX2+ progenitors were Ki67+, indicating active cell division in this region (data not shown).

The presence of a prominent oRGC-like population in day 84 forebrain organoids offers an opportunity to track the time course of oRGC marker expression during organoid development. A recent study showed that oSVZ-exclusive expression of HOPX, FAM107A, and PTPRZ1 does not occur in the developing human cortex until gestational weeks 15-20. Interestingly, very limited HOPX expression was detected in day 28 organoids, while at day 56 its expression was prominent in both VZ and SVZ, but not exclusive to SVZ (data not shown).

Together, these results demonstrate that forebrain organoids exhibit multi-layer progenitor zone organization that recapitulates human cortical development, including a prominent oSVZ layer with oRGC-exclusive expression of defined molecular markers. Our system provides a platform to investigate the origin, properties, and mechanisms that define and regulate human oRGCs.

Generation of Diverse Neuronal Subtypes of all Six Cortical Layers

Next, we performed detailed expression analyses of markers for different neuronal subtypes (data not shown). At day 28, we observed neurons expressing deep-layer cortical neuron markers CTIP2 and TBR1, as well as neurons expressing the Cajal-Retzius cell marker REELIN (data not shown). At days 56 and 70, the SVZ contained neurons expressing a low amount of CTIP2, a feature of migrating immature neurons found in this region (data not shown). The CP-like structure hosted a dense population of neurons expressing CTIP2 and TBR1, as well as a sparser population of neurons expressing upper-layer cortical neuron marker SATB2, which were localized close to the pial surface (data not shown). There was also a cell-sparse layer visualized by REELIN and DCX expression at the pial surface, resembling the marginal zone (MZ) that typically becomes layer I in vivo (data not shown). At day 84, late-born SATB2+ neurons formed a layer partially separated from the early-born CTIP2+ layer, suggesting specification of upper and deep cortical layers (data not shown). Furthermore, neurons expressing layer II/III markers CUX1 and BRN2 started to appear near the pial surface (data not shown). Quantification revealed CP and SVZ layer expansion and VZ layer reduction from days 56 to 84 (data not shown), resembling the developing human cortex.

Together, these results reveal the developmental time course of marker expression for neurons of all six cortical layers in forebrain organoids. Quantitative analysis of different organoids and human iPSC lines shows little variability in the relative thickness of different layers (data not shown), again indicating the robustness and reproducibility of our organoid system.

Molecular Signatures of Developing Forebrain Organoids

To further compare forebrain organoids to in vivo human brain development, we performed RNA-seq analyses of global transcriptomes from day 26, 40, 54, and 100 organoids. We compared organoid transcriptional profiles to datasets of 21 different human fetal organs during the first and second trimester. Pearson's correlation analysis showed that organoids from all four time points strongly correlated with fetal brains and spinal cord, with less or no correlation with other fetal somatic tissues (data not shown). Further comparison with transcriptomes from human dorsolateral prefrontal cortex samples across six life stages, ranging from fetal development to aged human tissue, showed the highest correlation with fetal brain tissues, with the best correlation for day 100 organoids (data not shown). Collectively, these results suggest that organoid development is reminiscent of fetal human brain development at the molecular level.

To pinpoint developmental stages and brain subregion identities of forebrain organoids, we performed large-scale comparisons with transcriptome datasets of 16 different human brain regions at 11 developmental stages (data not shown). These analyses revealed a temporal correlation between organoid and fetal human brain development, particularly for prefrontal cortex development (data not shown). For example, day 26-54 organoid profiles were closely related to several subregions of prefrontal cortex at 8-9 PCW (post-conception week), whereas day 100 organoids were more closely related to 17-24 PCW, or even 35 PCW for some subregions (data not shown).

We also identified differentially expressed genes during organoid development. These genes also displayed similar trends over the course of in vivo brain development (data not shown). Gene ontology analysis revealed enrichment of many neuronal function pathways among upregulated genes (data not shown) and enrichment of cell-cycle-related pathways among downregulated genes (data not shown). Interestingly, differentially expressed genes during organoid development and risk genes for schizophrenia or autistic spectrum disorders showed significant overlap ($p<0.001$, chi-square test). Therefore, the organoid system can be used to study the functional impact of dynamic expression of these disease risk genes in human brain development.

Together, our systematic and comprehensive transcriptome comparisons provide additional validation that forebrain organoids resemble normal human embryonic cortical development.

Functionally Connected Cortical Neurons and GABAergic Neuronal Subtypes

To assess physiological properties of cells in organoids, we performed electrophysiological whole-cell recording in slices acutely sectioned from organoids. Recorded neurons were capable of firing trains of TTX-sensitive action potentials (data not shown). Neurons showed rectifying membrane properties, Na+ and K+ currents in response to voltage ramps (data not shown). Cells with linear membrane properties were also observed, indicating presence of astrocytes (data not shown). We observed developmental changes of intrinsic properties in recorded neurons across different stages (data not shown).

To visualize morphology of individual neurons, we electroporated organoids to sparsely label cells with GFP. At day 85, GFP+ neurons exhibited complex neuronal morphology with spine-like structures in close association with presynaptic SV2+ puncta (data not shown). About 50% of cells recorded showed spontaneous excitatory postsynaptic current (sEPSC) that was sensitive to the glutamate receptor antagonist DNQX (data not shown). Both intrinsic properties and synaptic connectivity were similar between two iPSC clones (data not shown).

One hallmark of neuronal maturation is the switch from a depolarizing response to GABA to hyperpolarizing due to developmentally regulated changes in intracellular CP concentration, mediated by NKCC1 downregulation and KCC2 upregulation. We found that NKCC1 was expressed at both days 56 and 84, whereas KCC2 was strongly expressed in the CP at day 84 but minimally at day 56 (data not shown). We further performed a functional assay to monitor $Ca^{2+}$ rise in response to GABA-induced depolarization (data not shown). Quantification showed an increase over time in the percentage of neurons without GABA-induced $Ca^{2+}$ rise among all neurons that responded to glutamate (data not shown). Therefore, forebrain organoids exhibit functional features of neuronal maturation found in vivo.

We also found GABA+VGLUT1− neurons in forebrain organoids after day 84 (data not shown). Electrophysiological recordings in the presence of DNQX to block all glutamatergic synaptic transmission also showed spontaneous postsynaptic currents with slower kinetics (data not shown). Immunohistological analysis further revealed the presence of at least three major subtypes of GABAergic neurons expressing parvalbumin, nNOS, or somatostatin (data not shown). Consistent with electrophysiological recording results (data not shown), we observed S100p+ and GFAP+ astrocytes in close association with surrounding neurons (data not shown). Together, these findings demonstrate that forebrain organoids contain a diverse collection of neuronal and other cell types found in developing human brains.

Generation of Midbrain and Hypothalamic Organoids

We next explored approaches to generate organoids with other brain region identities. Building upon a 2D differentiation protocol for generating midbrain dopaminergic (DA) neurons, we applied Sonic hedgehog (SHH) agonists (recombinant SHH and Purmorphamine), FGF-8, SMAD inhibitors (SB431542 and LDN193189), and GSK3P inhibitor (CHIR99021) to induce floor-plate differentiation of human iPSCs, which were transferred to SpinΩ at day 14 (data not shown). At day 18, midbrain organoids showed organized neuroepithelium-like structures expressing NESTIN and floor-plate precursor marker FOXA2, but not DA neuron marker TH, whereas very few cells expressed forebrain marker PAX6 or hypothalamus progenitor marker RAX1 (data not shown). At day 38, we observed numerous TH+ DA neurons (data not shown). At day 56, the majority of TH+ neurons expressed FOXA2+ and dopamine transporter (DAT) (data not shown). In addition, midbrain organoids contained TH+ cells that expressed midbrain DA neuron markers NURR1 and PITX3 (data not shown). At day 75, PITX3 was robustly expressed by TH+ cells, suggesting specification of A9 DA neurons (data not shown). To quantify TH and FOXA2 expression, we dissociated midbrain organoids at day 65. Upon culturing in monolayer for 5 days, we found that 95%±1% of cells were FOXA2+ and 55%±4% were TH+DA neurons (n=6; data not shown).

We also explored methods to generate hypothalamic organoids from human iPSCs. We first treated human iPSCs with dual SMAD inhibitors (SB431542 and LDN193189) to pre-pattern them to the neuroectodermal fate (data not shown). After 3 days, embryoid bodies were treated with WNT3A, SHH, and Purmorphamine to induce the hypothalamic lineage. At day 8, the majority of cells in organoids expressed NKX2.1, NKX2.2, RAX1, SOX2, NESTIN, and FOXA2, markers that are consistently expressed during early hypothalamus development (data not shown). At day 40, peptidergic neuronal markers, including POMC, VIP, OXT, and NPY, were detected in organoids generated from different iPSC lines (data not shown). At day 40, but not day 8, a subset of cell populations expressed OTP, a homeobox protein essential for specification of hypothalamic neuronal lineages (data not shown). Together, these findings demonstrate the versatility of SpinΩ to support growth of organoids of different types.

Modeling ZIKV Exposure During Cortical Neurogenesis

Our organoid system provides a quantitative platform to model human diseases. The World Health Organization recently declared ZIKV a Public Health Emergency of International Concern, due in part to the uncertainty surrounding increased reports of microcephaly and other neurological disorders coinciding with clusters of ZIKV outbreaks. Recent studies of human NPCs in 2D and neurosphere cultures showed efficient infection by ZIKV, leading to increased cell death and attenuated growth. Without organizational features unique to 3D brains, such as cortical layers, these initial studies in 2D cultures do not directly address the potential link between ZIKV and microcephaly. It also remains unknown whether ZIKV exhibits specific tropism for different neural cell types in more complex 3D tissue.

We performed a series of experiments to model transient ZIKV exposure at different stages of human cortical development by incubating forebrain organoids with ZIKV in medium for 24 hr in Spina. We initially used a prototype ZIKV strain of African lineage (MR766, termed ZIKV$^M$ hereafter). ZIKV$^M$ readily infected SOX2+NPCs in day 14 forebrain organoids (data not shown). After 18 days, ZIKV$^M$ infection resulted in overall decreased organoid size (data not shown). Quantitative analyses showed dramatically reduced VZ thickness and size (data not shown), likely due to significant cell death and suppression of NPC proliferation (data not shown). We also observed a significant increase in lumen size within ventricular structures (data not shown), reminiscent of dilated ventricles in a recently reported clinical case of a fetal brain infected with ZIKV.

Next, we exposed day 28 organoids that contained both progenitor and neuronal layers to two different doses of ZIKV$^M$. Most ZIKV$^M$-infected cells were SOX2+ NPCs, and very few were TBR2+ IPCs or CTIP2+ immature neurons when quantified 4 days later (data not shown), suggesting specific tropism of ZIKV$^M$ toward NPCs in the 3D tissue. After 14 days, we observed a significantly increased number of ZIKV$^M$-infected cells (data not shown), consistent with productive infection by ZIKV. In addition to overall size reduction (data not shown), we observed a ZIKV dose-dependent decrease of EdU+-proliferating cells and increased CAS3+ cells (data not shown). Interestingly, many CAS3+ cells were ZIKV$^-$, indicating a non-cell-autonomous effect (data not shown). As a result, ZIKV infection of early stage organoids, corresponding to the first trimester of human fetal development, led to a significant reduction in both VZ and neuronal layer thickness (data not shown), resembling microcephaly.

We also assessed the effect of ZIKV$^M$ on day 80 forebrain organoids (data not shown). After 10 days, we again observed preferential localization of ZIKV$^M$ in SOX2+ NPCs in VZ and oSVZ, but it was also detected in CTIP2+ neurons and occasionally in GFAP+ astrocytes (data not shown). The infection appeared less robust compared to that of earlier stages of organoids, possibly due to limited ZIKV penetration to the interior of organoids where NPCs reside. After 20 days, we observed an increased number of ZIKV+ cells (data not shown). Quantification showed a higher percentage of SOX2+NPCs with ZIKV$^M$ than that for CTIP2+ neurons (data not shown). The presence of ZIKV+ SOX2+HOPX+ cells indicates infection of oRGCs by ZIKV (data not shown).

Two recent studies have shown few differences between properties of different ZIKV strains in different models. We explored a ZIKV strain of Asian lineage that exhibits>99% amino acid sequence similarity to strains currently circulating in Brazil (FSS13025, termed ZIKV$^C$ hereafter). Quantitative analysis showed similar enrichment of ZIKV$^C$ in SOX2+NPCs, compared to CTIP2+ immature neurons or TBR2+IPCs in early stage organoids (data not shown).

Together, our forebrain organoid system allowed quantitative investigation of consequences of ZIKV exposure, and our results suggest that ZIKV, upon access to the fetal brain, targets NPCs and causes microcephalic-like deficits in cortical development.

Discussion

We have developed a cost-effective, simple-to-use system for 3D organoid cultures by designing a miniaturized multi-well spinning bioreactor, SpinΩ, which can be used with standard cell-culture plates. The low cost of the platform allowed us to optimize protocols to generate forebrain organoids with minimized heterogeneity and variability that enables quantitative analyses and better recapitulation of the developing human cortex. Specifically, these forebrain organoids exhibit a well-developed oSVZ-like region containing NPCs that share molecular and morphological features of human oRGCs, organized neuronal subtypes found in all six cortical layers, and GABAergic neuronal subtypes. We further demonstrated SpinΩ's versatility by developing protocols to generate organoids recapitulating characteristics of other brain regions. Finally, we applied our forebrain organoid platform for chemical compound testing and modeling ZIKV infection.

SpinΩ, a Miniaturized Spinning Bioreactor for Cost-Effective Organoid Culturing

Several pioneering studies showed that cerebral organoid systems offer improved growth conditions for 3D tissue, leading to a more representative model of the developing human brain. In particular, the use of a spinning flask provides a 3D low-shear stress suspension culture with enhanced diffusion of oxygen and nutrients that supports formation of larger, continuous cortical structures. Under our culture conditions, direct comparison with stationary and orbital shaker cultures confirmed the beneficial effect of spinning for forebrain organoids. However, maintaining organoids in standard spinning flasks makes it cost prohibitive to supplement the media with small molecules and growth factors to promote growth and differentiation of organoids. Our miniaturized spinning bioreactor SpinΩ addresses this limitation by dramatically reducing the required media volume, allowing for systematic and efficient testing of culture conditions in parallel. Moreover, SpinΩ's small footprint and compact shape reduces the incubator space required, a feature that is further highlighted by the stackable version. Many of the design parameters of SpinΩ, including number and size of wells, rotation speed, shaft angle, and shape, can be customized based on specific needs. Together, the SpinΩ system provides better accessibility and higher efficiency for developing 3D tissue cultures for applications related to the brain and other organs.

Features of Forebrain Organoids and Areas for Improvements

Compared to several pioneering cerebral organoid systems, our forebrain organoids show high reproducibility, which is critical to realize its promise as a standardized model for human cortical development. Two rounds of patterning factors effectively induce forebrain differentiation and significantly reduce both tissue and temporal development heterogeneity. Our proof-of-principle study with BPA, although with concentrations likely higher than normal human exposure, demonstrates that many parameters in these organoids can be reliably quantified; therefore, this platform can be broadly used for drug testing, compound screening, and disease modeling.

Forebrain organoids better recapitulate developing human cortex along multiple dimensions, as compared to previously reported methods. First, these forebrain organoids contain a well-defined oSVZ-like region with a prominent oRGC-like NPC layer, which are distinct features of developing human cortex that are absent in rodents and previous organoid models. Time course of SVZ and oSVZ layer formation and progression also models dynamic changes during human cortical development. Moreover, oRGCs in forebrain organoids express three recently identified human oRGC markers. Second, forebrain organoids robustly generate organized cortical neurons expressing markers found in all six layers of human cortex, including a layer of CUX1+ neurons destined for layer II. The peak in production of late-born neurons expressing the upper-layer neuron marker SATB2 occurred after day 56, coinciding with oSVZ specification and expansion. Because the peak of oSVZ proliferation coincides in time with formation of upper cortical layers, which are particularly cell dense in human cortex, it has been suggested that the abundant oRGC population in human oSVZ is responsible for this evolutionary distinction. Therefore, the presence of well-developed oSVZ may be responsible for robust generation of upper-layer neurons in forebrain organoids. Our electrophysiology and calcium imaging analyses revealed functional neuronal properties, active synaptic transmission, and recapitulation of neuronal maturation characteristics similar to those observed in vivo. We show the presence of GABAergic neuronal subtypes in organoids. The apparent absence of NKX2.1+ ventral progenitors during early differentiation suggests a possible dorsal origin of GABAergic neurons, a distinct feature of primates and humans. Lastly, large-scale comparisons of global transcriptome analyses confirm that forebrain organoid development closely correlates with human cortical development at the molecular level. Forebrain organoids with a well-developed oSVZ will significantly expand our ability to study distinct characteristics of human cortical development that cannot be represented in rodent models. Compared to studies of postmortem human tissues, forebrain organoids offer a model to investigate embryonic human cortical development as a continuous dynamic process in live cells and allow pharmacological and genetic manipulations to investigate underlying mechanisms.

It is likely that continued optimization can further improve the forebrain organoid system. First, depletion of nutrients and oxygen in the interior of organoids is one factor limiting our ability to model human brain development beyond the second trimester. Due to dramatic CP expansion, progenitor zones in forebrain organoids become gradually depleted after day 100. One potential solution is to engineer vascularized 3D tissue by endothelial cell co-cultures or by implementing microfluidic perfusion networks. An alternative approach would be to explore culture conditions that can accelerate forebrain organoid development to produce features of late-stage cortical development with smaller overall organoid size. Second, forebrain organoids do not contain well-defined regions representing the intermediate zone (IZ) and subplate, which play important roles in neuronal migration during cortical development. Intriguingly, a previously reported cortical neuroepithelial system showed formation of a cell-sparse IZ-like region despite lacking oSVZ. Third, although we have identified cortical neurons expressing markers found in all six human cortical layers, they display only rudimentary separation. Additional chemical and physical cues may be required to better regulate neuronal migration and positioning.

Modeling ZIKV Exposure During Different Stages of Cortical Neurogenesis

As an application of our organoid platform for disease modeling, we modeled the impact of ZIKV exposure at different stages of pregnancy. Recent clinical studies have established that ZIKV can pass through placenta to gain access to the developing fetal brain. We show that, among different cell types in 3D tissue, ZIKV exhibits specific tropism toward NPCs, including oRGCs, although ZIKV could be detected in immature neurons, IPCs, and astrocytes. Time-course analysis further shows that ZIKV infection in NPCs is productive, resulting in more infected cells over time. Therefore, even a very low-dose and transient ZIKV exposure in utero may have a prolonged and increasingly severe effect over time. Consistent with clinical findings that first trimester infections are the most dangerous, exposure of early stage forebrain organoids to ZIKV for only 1 day leads to detrimental effects, mimicking many features of microcephaly, including decreased neuronal layer thickness and overall size as well as enlarged lumen/ventricles. Mechanistically, we show increased cell death and suppressed proliferation of infected NPCs. The same ZIKV treatment of day 80 organoids, which are more complex and resemble the second trimester, also leads to preferential infection of SOX2+ NPCs, including HOPX+ oRGCs. Together, our results provide compelling evidence that, upon access to the fetal brain, productive and preferential infection of NPCs by ZIKV leads to characteristic features resembling microcephaly. Forebrain organoids therefore provide a quantitative experimental platform for future studies to investigate the impact of ZIKVs, identify cellular and molecular mechanisms, and screen for therapeutic interventions, issues that are critical to resolving the current global health emergency related to ZIKV.

Additional Future Applications

Brain organoids also provide a renewable source of human neurons and other cell types, such as DA neurons for transplantation in models of Parkinson's disease. Organoid growth is coupled with dramatic expansion in cell numbers. For example, embryoid bodies of around 300 mm in diameter could expand to organoids that are up to 3 mm in diameter, achieving a 1,000-fold expansion in cell mass. Just as the cerebral organoid methodology was inspired by self-organizing tissue organoids developed for other organs, SpinΩ has the potential to be broadly applied to other types of 3D tissue cultures beyond the nervous system, where SpinΩ's advantages in reduced cost, increased throughput, enhanced cell survival, and improved factor absorption would prove beneficial. The modular stackable version of SpinΩ allows for consistent culture conditions for multiple plates simultaneously and potential large-scale 3D tissue cultures and drug screening.

Experimental Procedures

Bioreactor Design and 3D Printing

We used SolidWorks™ for design and drawings of all components for 3D printing. Modular individual bioreactors were made to fit into a stackable bioreactor with some modifications.

Culture of Brain-Region-Specific Organoids, Immunohistology, and Quantification

All studies were performed with approved protocols of Johns Hopkins University School of Medicine. Human iPSC lines were previously characterized. See detailed protocols to generate forebrain, midbrain, and hypothalamic organoids in the Supplemental Experimental Procedures.

Whole organoids were processed for immunocytochemistry, as previously described. For cell-fate quantifications of day 14 organoids, neural tube structures were counted as positive for forebrain markers when >80% of all nuclei were positive for respective markers. Markers for different brain regions were quantified by measuring the area stained positive for markers and normalized to DAPI in ImageJ software. VZ was defined by SOX2 immunoreactivity and neural-tube morphology, and the outer layer was defined by the area outside of the VZ to the nearest pial surface. The relative VZ thickness was defined as the ratio of VZ thickness to VZ plus outer layer thickness. Layer thickness measurements at days 56 and 84 in forebrain organoids were performed similarly with the addition of SVZ. SVZ was defined by the region within mixed populations of SOX2+ and CTIP2+ nuclei outside of VZ. CP was defined by the region from the boundary of SVZ to the pial surface with exclusive CTIP2+ nuclei. Some sample images shown were from tiling multiple images of a large area as indicated.

RNA-Seq and Bioinformatics Analyses

Forebrain organoids at days 26, 40, 54, and 100 were processed for RNA-seq and bioinformatics analyses, as previously described. Sequence read counts for 22 different human fetal organs were obtained from GSE66302. Human dorsolateral prefrontal cortex RNA-seq datasets from six different life stages were obtained from nature.com/neuro/journal/v18/n1/extref/nn.3898-S9.zip. RNA-seq gene expression for 11 time points of fetal development and 16 different brain regions were obtained from Allen Brain Atlas (brain-map.org). Schizophrenia-related risk genes were obtained from bioinfo.mc.vanderbilt.edu/SZGR. Autism-related risk genes were obtained from gene.sfari.org/autdb/HG_Home.do. R programming language was used to perform all data analysis and generate the figures.

Electrophysiology and Calcium Imaging

Organoid slices were prepared by embedding organoids in 4% low melting point agarose cooled to ~32° C. Slices (250 mm) were sectioned and were immediately ready for recording. Calcium imaging was performed similarly, as previously described.

Modeling ZIKV Exposure

ZIKV was prepared and titered as previously described. Supernatant from ZIKV-infected mosquito C6/36 cells (ZIKV$^M$) or Vero cells (ZIKV$^C$) was diluted 1:10 (1×) or 1:40 (0.25×) and applied directly in SpinΩ for 24 hr and then replaced with fresh medium. Forebrain organoids infected at day 28 were pulsed with 10 mM EdU for 2 hr on day 42 and were fixed for analysis 24 hr later. Quantitative analyses were conducted on randomly picked cortical structures. Cell death was quantified by counting CAS3+ nuclei over total nuclei stained by DAPI. Area of VZ and lumen and thickness of VZ and neuronal layers were measured using ImageJ software. Overall size of organoids was measured under calibrated 4× bright field microscope.

Accession Numbers

The accession number for RNA-seq data reported herein is GEO: GSE80073 which is incorporated herein by reference in its entirety.

Supplemental Information

Bioreactor Design, 3D Printing and Assembling

We used SolidWorks' for design and drawings of all parts, including spinning leaf and shafts. Cover units were designed to fit a standard 12-well culture plate. Autoclavable plate cover and spinning shafts were printed with a 3D printer (Fortus™ 450mc) using ULTEM™ 9085, and other parts were printed using polycarbonate. Standalone spinning bioreactors were assembled from parts consisting of IG16 6 VDC 051 RPM Gear Motor (SuperDroid Robots™ TD-060-051), gears (GR.MOLD.SP.M0.5 (US); SDP/SIA 1Z 2MYZ0505206), sleeve bearings (Metric PTFE Sleeve Bearing, for 6 mm Shaft Diameter, 12 mm OD, 10 mm Length; McMaster-Carr 2685T11), Aluminum Unthreaded Spacers (¼" OD, ¾" Length, #4 Screw Size; McMaster-Carr 92510A308), and a power supply (Hosa Cable ACD477 Universal AC Power Supply; Amazon®). The modular individual bioreactors were made to fit into a stackable bioreactor with some modifications. All gears in the stackable bioreactor were driven by motor with higher output (IG32 Right Angle 12 VDC 043 RPM Gear Motor; SuperDroid Robots' TD-035-043) connected to a series of shaft couplings (Rigid, Setscrew; Misumi CPR16-6-6), rotary shafts (D Cut; Misumi SSFRV6-55-F19-T12), bearings (Single Row, Metric Sizes, Acetal Plastic Radial Ball Bearings fitted with Glass Balls; KMS Bearings A626-G), and gears (Module 0.5, 96 Teeth, 20° Pressure Angle, Acetal/Brass Insert Spur Gear (SDP/SIA 1Z 2MYZ0509606).

Maintenance of Human iPSCs

Human iPSC lines used in the current study were previously fully characterized. They were cultured in stem cell medium, consisting of DMEM:F12 (Invitrogen) supplemented with 20% Knockout™ Serum Replacer (Gibco), 1× Non-essential Amino Acids (Invitrogen), 1× Penicillin/Streptomycin (Invitrogen), 1×2-Mercaptoenthanol (Millipore), 1× Glutamax (Invitrogen), and 10 ng/ml FGF-2 (Peprotech) as previously described (Yoon et al., 2014). Culture medium was changed every day. Human iPSCs were passaged every week onto a new plate pre-seeded with irradiated CF1 mouse embryonic fibroblasts (Charles River). iPSCs were detached from the plate by treatment of 1 mg/ml Collagenase Type IV (Invitrogen) for 1 hr. iPSC colonies were further dissociated into smaller pieces by manual pipetting. All studies were performed with approved protocols of Johns Hopkins University School of Medicine.

Culture of Forebrain Organoids from Human iPSCs

To generate forebrain-specific organoids, human iPSC colonies were detached 7 days after passage with Collagenase Type IV, washed with fresh stem cell medium and cultured in a 15 ml conical tube. On day 1, detached and washed iPSC colonies were transferred to an Ultra-Low attachment 6-well plate (Corning Costar), containing 3 ml of stem cell medium (without FGF-2), plus 2 μM Dorsomorphine (Sigma) and 2 μM A83-01 (Tocris). On days 5-6, half of the medium was replaced with induction medium consisting of DMEM:F12, 1×N2 Supplement (Invitrogen), 10 μg/ml Heparin (Sigma), 1× Penicillin/Streptomycin, 1× Non-essential Amino Acids, 1× Glutamax, 4 ng/ml WNT-3A (R&D Systems), 1 μM CHIR99021 (Cellagentech), and 1 μM SB-431542 (Cellagentech). On day 7, organoids were embedded in Matrigel (BD Biosciences) and continued to grow in induction medium for 6 more days. On day 14, embedded organoids were mechanically dissociated from Matrigel by pipetting up and down onto the plate with a 5 ml pipette tip. Typically, 10-20 organoids were transferred to each well of a 12-well spinning bioreactor (FIGS. 1-11) containing differentiation medium, consisting of DMEM:F12, 1×N2 and B27 Supplements (Invitrogen), 1× Penicillin/Streptomycin, 1×2-Mercaptoenthanol, 1× Non-essential Amino Acids, 2.5 μg/ml Insulin (Sigma). At day 71, differentiation medium was exchanged with maturation medium, consisting of Neurobasal (Gibco), 1× B27 Supplement, 1× Penicillin/Streptomycin, 1×2-Mercaptoenthanol, 0.2 mM Ascorbic Acid, 20 ng/ml BDNF (Peprotech), 20 ng/ml GDNF (Peprotech), 1 ng/ml TFGp (Peprotech), and 0.5 mM cAMP (Sigma). The organoids could grow beyond 110 days in maturation medium. All media were changed every other day. For the stationary culture, day 14 organoids were generated following the same protocol and then maintained in an Ultra-Low attachment 6 well plate (Corning Costar) with differentiation media. The "intrinsic protocol" for differentiation of human iPSCs into cerebral organoids followed the published protocol.

Culture of Midbrain Organoids from Human iPSCs

To generate midbrain-specific organoids, human iPSC colonies were detached with Collagenase Type IV 7 days after passage and washed with fresh stem cell medium in a 15 ml conical tube. On day 1, the detached and washed iPSC colonies were transferred to an Ultra-Low attachment 6-well plate containing EB medium, consisting of DMEM:F12, 15% Knockout™ Serum Replacer, 1× Glutamax, 1×2-Mercaptoenthanol, 100 nM LDN-193189, 10 μM SB-431542, 100 ng/ml SHH (Peprotech), 2 μM Purmorphamine (Stemgent), 100 ng/ml FGF-8 (Peprotech). On day 5, EB medium was gradually switched to SHH medium, consisting of DMEM:F12, 1×N2 Supplement, 1× Glutamax, 100 nM LDN-193189, 3 μM CHIR99021, 100 ng/ml SHH, 2 μM Purmorphamine, 100 ng/ml FGF-8. On day 7, SHH medium was replaced with induction medium, consisting of DMEM:F12, 1×N2 Supplement, 1× Glutamax, 100 nM LDN-193189, 3 μM CHIR99021. On day 14, 10-20 organoids were transferred to SpinQ with differentiation medium, consisting of Neurobasal, 1× B27 Supplement, 1× Glutamax, 1×2-Mercaptoenthanol, 20 ng/ml BDNF, 20 ng/ml GDNF, 0.2 mM Ascorbic Acid, 1 ng/ml TGFp, and 0.5 mM c-AMP. All media were changed every other day.

Culture of Hypothalamus Organoids from Human iPSCs

To generate hypothalamus-specific organoids, human iPSC colonies were detached 7 days following passaging with Collagenase Type IV, and washed with fresh stem cell medium in a 15 ml conical tube. On day 1, detached and washed iPSC colonies were transferred to an Ultra-Low attachment 6-well plate (Corning Costar) containing stem cell medium. One day after (day 2), stem cell medium was replaced with induction medium A, consisting of DMEM:F12, 10% Knockout™ Serum Replacer, 1× Non-essential Amino Acids, 1× Penicillin/Streptomycin, 1×2-Mercaptoenthanol, 1× Glutamax, 2.5 µM LDN-193189 (Stemgent), 3 µM SB-431542, and 450 µM 1-Thioglycerol (Sigma). On day 4, the medium was switched to induction medium B, consisting of DMEM:F12, 10% Knockout™ Serum Replacer, 1× Non-essential Amino Acids, 1× Penicillin/Streptomycin, 1× Glutamax, 1×N2 Supplement, 10 ng/m Wnt-3A, 20 ng/ml SHH, and 2 µM Purmorphamine. On day 7, 5-10 organoids were transferred to a 12-well spin bioreactor and induction medium B was replaced with differentiation medium, consisting of DMEM:F12/Neurobasal (1:1 ratio), 1× B27 Supplement, 1× Non-essential Amino Acids, 1× Penicillin/Streptomycin, 1× Glutamax, 10 ng/ml FGF-2 and 10 ng/ml CTNF (Peprotech). Media were changed every other day.

Tissue Preparation and Immunohistochemistry

Whole organoids were fixed in 4% Paraformaldehyde in Phosphate Buffered Saline (BPS) for 30-60 min at room temperature. Organoids were washed 3 times with PBS and then incubated in 30% sucrose solution overnight. Organoids were embedded in tissue freezing medium (General Data) and sectioned with a cryostat (Leica). For immunostaining, freezing medium was washed with PBS before permeablization with 0.2% Triton-X in PBS for 1 hr. Tissues were blocked with blocking medium consisting of 10% donkey serum in PBS with 0.1% Tween-20 (PBST) for 30 min. Primary antibodies diluted in blocking solution were applied to the sections overnight at 4° C. After washing with PBST, secondary antibodies diluted in blocking solution were applied to the sections for 1 hr at room temperature. Finally, sections were washed with PBST and stained with DAPI. All images were captured by a confocal microscope (Zeiss™ LSM 700). For paraffin-embedded human samples, slides were first deparaffinized and retrieved using sodium citrate heated to boil in a microwave oven and immunostained as above. Some sample images shown were from tiling multiple images of a large area.

BPA Treatment Experiment

Forebrain organoids were grown using the protocol described above. For the long-term BPA treatment experiment, forebrain organoids at day 14 from the same batch were distributed randomly into separate wells within SpinQ and treated with different concentrations of BPA (Sigma). BPA was dissolved in sequential dilutions in differentiation media with 0.05% methanol, which was also added in the control condition. Media containing BPA was replaced every other day until analysis on day 28. A previous study determined that tissue culture plates do not contain detectable BPA. Quantification was conducted by investigators blind to culture conditions.

For the acute BPA treatment experiment, forebrain organoids were grown to day 28 and treated with corresponding concentrations of BPA for 24 hr. At day 29, the culture media was replaced with fresh media and washed 3 times to remove residual BPA. Organoids were then pulsed with 10 µM EdU for 2 hr. The media was then replaced and organoids were washed 3 times with fresh media. At day 30, organoids were fixed for immunohistochemistry and EdU detection using Click-iT® EdU Alexa Fluor® 488 Imaging Kit (ThermoFisher C10337) according to the manufacturer's manual, followed by immunostaining for SOX2 and PH3. Images were acquired with a Zeiss' LSM 700 Confocal system at 25× magnification. Quantification was performed by counting the number of EdU and PH3+ nuclei within SOX2+ ventricular structures that were defined by neural tube-like morphology. EdU and PH3 densities were normalized to the area of ventricular structures measured in ImageJ software. Quantification was conducted by investigators blind to culture conditions.

Quantification of Cell Fates and Layer Thickness

For cell fate quantifications, organoids grown from the "intrinsic protocol" and forebrain protocol were immunostained for SOX2, PAX6 and OTX2 at day 14. Images were acquired with a Zeiss' Axiovert 200M fluorescent microscope. Neural tube structures were counted as positive for forebrain markers when more than 80% of all nuclei were positive for respective markers. Markers for different brain regions (FOXA2, NKX2.1 and PROX1) were quantified by measuring the area stained positive for markers and normalized to DAPI in ImageJ™ software.

Organoids grown from the "intrinsic protocol" and forebrain protocol were immunostained for SOX2, TUJ1 and CTIP2 at days 14 and 28. The ventricular-like zone (VZ) was defined by SOX2 immunoreactivity and neural-tube morphology and the outer layer was defined by the area outside the VZ to the nearest pial surface. For each ventricular structure, 3 measurements were performed forming a right angle fan area pointing to the nearest pial surface, at 0, 45 and 90 degrees. The length for VZ and outer layer was measured in ImageJ™ software. The relative VZ thickness was defined as the ratio of VZ thickness to VZ plus outer layer thickness. Layer thickness measurements at days 56 and 84 in forebrain organoids were performed similarly as described above with the addition of SVZ. The SVZ was defined by the region within a mixed population of SOX2+ and CTIP2+ nuclei outside the VZ. The cortical plate (CP) was defined by the region from the boundary of SVZ to the pial surface within exclusive CTIP2+ nuclei. Relative thicknesses for VZ, SVZ and CP were calculated by the ratio to total thickness from ventricular to pial surface.

RNA-Seq and Bioinformatics Analyses

Forebrain organoids at days 26, 40, 54 and 100 (three samples for the first three time points and two samples for day 100) were collected and processed for RNA-seq and bioinformatics analyses as previously described.

Sequence read counts for 22 different human fetal organs were obtained from GSE66302. The sequences were aligned to UCSC hg19 reference genome using tophat v2.0.13, and the read counts were obtained using R/Bioconductor). Human dorsolateral prefrontal cortex RNA-seq datasets (RPKM values) from six different life stages were obtained from nature.com/neuro/journal/v18/n1/extref/nn.3898-S9.zip. RNA-seq gene expression (RPKM) for 11 time points of fetal development and 16 different brain regions were obtained from Allen Brain Atlas™. All gene expression values are summarized as the log RPKM values against the Ensembl gene annotation.

To quantify gene expression correlation between organoids from the current study and fetal organs, we first selected genes with moderately high average expression levels and variance. Briefly, we only used genes with average expression levels greater than three and variance greater than one from fetal organs. These genes show marked differences among organs and thus are more informative than using all genes in the correlation analysis. Pearson correlations were computed based on expression of these genes. Correlations were averaged for biological replicates. We found that the patterns of correlation were stable against the gene selection criteria. Thresholds used for selecting genes, albeit arbitrary, had very little impact on the final results. The same strategy was used to compute the correlations between organoid and other samples (brains at different developmental stages and regions).

Differentially expressed genes between day 26 and late stages of organoids were defined as genes with absolute log fold changes of RPKM greater than one, and average baseline expression (log RPKM) greater than 2. Schizophrenia-related risk genes were obtained from Schizophrenia Gene Resource (SZGR). Autism-related risk genes were obtained from Simons Foundation Autism Research Initiative (SFARI). The significance of gene overlap was assessed by chi-squared test on 2-by-2 tables. R programming language was used to perform all data analysis and generate the figures.

Electroporation

Organoids at day 50 were transferred into Petri dishes containing PBS, and 2 µl of GFP expressing plasmid (pCAGGS-eGFP, 2 µg/µl, diluted in sterile PBS with 0.01% fast green) was injected into 3-4 locations within an organoid using a beveled and calibrated micropipette. Five pulses (40 V, 50 ms in duration with a 950 ms interval) were delivered with tweezer electrodes (CUY650-5, Nepa Gene) by a CUY21SC electroporator (Nepa Gene) as previously described. Electroporated organoids were transferred back to SpinQ and cultured until fixation.

Electrophysiology

Organoid slices were prepared by embedding organoids in 4% low melting point agarose cooled to approximately 32° C. Slices (250 µm) were sectioned using a vibratome (Microm™ HM650V) and stored at room temperature, oxygenated (95% $O_2$, 5% $CO_2$) artificial cerebrospinal fluid (ACSF) containing (in mM): 125 NaCl, 25 NaHCO$_3$, 1.25 NaH2PO$_4$, 3 KCl, 25 dextrose, 1 MgCh, and 2 CaCl$_2$, pH 7.3. Slices were immediately ready for recording.

ACSF was oxygenated (95% $O_2$, 5% $CO_2$) and bath temperature was approximately 38° C. Patch pipettes were fabricated from borosilicate glass (N51A, King Precision Glass, Inc.) to a resistance of 2-5 MQ. For current- and voltage-clamp measurements, pipettes were filled with (in mM): 125 potassium gluconate, 10 HEPES, 4 Mg-ATP, 0.3 Na-GTP, 0.1 EGTA, 10 phosophocreatine, 0.05%, adjusted to pH 7.3 with KOH. For all experiments, GABAa receptors were blocked with SR-95531 (Gabazine, 5 µM, Abcam). In sEPSC experiments, synaptic currents were blocked with 6,7-Dinitroquinoxaline-2,3-dione (DNQX, 10 µM, Abcam). Sodium currents and action potentials were blocked with tetrodotoxin (TTX, 300 nM, Abcam). Current signals were recorded with either an Axopatch™ 200B (Molecular Devices) or a Multiclamp™ 700A amplifier (Molecular Devices) and were filtered at 2 kHz using a built in Bessel filter and digitized at 10 kHz. Voltage signals were filtered at 2 kHz and digitized at 10 kHz. Data were acquired using Axograph on a Dell® PC (Windows® 7). For voltage clamp recordings, cells were held at −70 mV.

Calcium Imaging Analysis

Calcium imaging was performed similarly to previous descriptions. Organoids were loaded with Fluo-4 (Life Technologies) for 30 min before the start of imaging. Throughout experiments, oxygenated aCSF was continuously perfused at a rate of 3 ml/min at room temperature (25±2° C.). Glutamate and GABA were added to media during imaging sessions at a final concentration of 20 µM and 10 µM, respectively. Bicuculline was added by bath application to media during imaging at a final concentration of 50 µM and imaging was resumed after a 15-min incubation time. Cells were excited at 488 nm, and Fluo-4 signal was collected at 505-550 nm. Images were acquired and analyzed using NIH Image J™ software. The $Ca^{2+}$ signal change was determined by AF/F [AF/F=[(F1−B1)−(F0−B0)]/(F0−B0)], which was normalized to the mean fluorescence intensity measured at the baseline condition (set as 0%).

Modeling ZIKV Exposure

ZIKV was prepared and titered as previously described. Supernatant from ZIKV$^M$ infected mosquito C6/36 or ZIKV$^C$ infected Vero cells was diluted 1:10 (1×) or 1:40 (0.25×) into forebrain organoid differentiation media, and applied directly to forebrain organoids in SpinQ. The virus inoculum was removed after a 24 hour incubation in spinning culture and replaced with fresh medium. Forebrain organoids infected at day 28 were pulsed with 10 µM EdU for 2 hours on day 42, and fixed for analysis 24 hours later. Quantitative analyses were conducted on randomly selected cortical structures captured by confocal microscope (Zeiss™ LSM 700). Cell proliferation was measured by density of PH3+ or EdU+ nuclei in ventricular structures similar to those described in BPA experiments. Cell death was quantified by counting activated caspase-3+ nuclei over total nuclei stained by DAPI. Area of VZ and lumen, and thickness of VZ and neuronal layers were measured using ImageJ software. Overall size of organoids was measured under a calibrated 4× bright field microscope.

Example 3

Zika-NS2A Reduces Cortical Neural Stem Cell Proliferation and Disrupts Adherens Junction Formation Zika, but not Dengue, virus NS2A protein disrupts cortical neurogenesis. Zika virus (ZIKV)-induced microcephaly represents a global health emergency. ZIKV infects neural stem cells (NSCs), but how ZIKV interacts with the NSC host machinery to impact brain development is unknown. Here, by systematically introducing individual proteins encoded by ZIKV into radial glia cells in embryonic mouse cortex, we show that expression of ZIKV-NS2A, but not Dengue virus NS2A, leads to reduced proliferation and depletion of NSCs. We mapped NS2A protein-interactomes across the human proteome. Interestingly, ZIKA-NS2A interacts with and destabilizes the adherens junction complex, resulting in impaired adherens junction formation in embryonic mouse cortex. Similarly, ZIKA-NS2A expression leads to reduced radial glia cell proliferation and adherens junction deficits in human forebrain organoids. Together, our study reveals mechanisms underlying ZIKV pathogenesis in the developing mammalian brain.

The recent outbreak of ZIKV, a flavivirus transmitted via multiple routes, is an ongoing global health emergency. Of greatest concern is the link between ZIKV infection during pregnancy and congenital neurodevelopmental birth defects, including microcephaly. ZIKV has been shown to directly infect cortical NSCs and cause proliferation deficits and cell death, findings cited by the US Center for Disease and Control as biological plausibility to declare that ZIKV causes microcephaly. While studies have revealed dysregulated signaling pathways in cultured NSCs upon ZIKV infection, nothing is known about how ZIKV directly interacts with the host machinery to impact neurogenesis in developing mammalian cortical tissue.

ZIKV, a positive sense single-stranded RNA virus, encodes for a polyprotein that is subsequently cleaved into three structural proteins (C, prM, and E) and multiple nonstructural proteins (NS1, NS2A, NS2B, NS3, NS4A, NS4B and NS5). We took an unbiased and systematic approach to screen for ZIKV protein component(s) that may affect cortical neurogenesis in vivo. We cloned each open reading frame of ZIKV into an expression vector and co-expressed individual ZIKV proteins and GFP in E14.5 embryonic mouse cortex via in utero electroporation. We pulsed animals with EdU at E17.5 and examined the percentage of EdU+ cells among GFP+Pax6+ radial glia cells 2 hours later as the proliferation index for the initial screen (data not shown). We found the most dramatic effect in the reduction of the proliferation index for ZIKV-NS2A and a mild effect for ZIKV-C (data not shown).

We next focused on ZIKV-NS2A for detailed analyses. ZIKV-NS2A exhibit 95.6-99.9% identity at the protein level among different ZIKV strains, suggesting a highly conserved protein. Quantitative analysis showed that ZIKV-NS2A expression led to a reduction in the percentage of EdU+ cells among all GFP+ cells or GFP+Pax6+ radial glia cells compared to GFP expression alone, indicating a proliferation deficit (data not shown). The percentage of GFP+Pax6+ cells among all GFP+ cells was also reduced, suggesting depletion of radial glia cells in the developing mouse cortex (data not shown). Radial glia cells give rise to Tbr2+ intermediate neural progenitor cells (IPCs). We found that ZIKV-NS2A expression also reduced the percentage of EdU+ cells among GFP+Tbr2+ IPCs (data not shown). These results are reminiscent of the impact of direct ZIKV infection on neurogenesis in the embryonic mouse cortex. In addition, ZIKV infection leads to increased cell death of NSCs. We found that ZIKV-NS2A expression led to a small, but significant increase in the percentage of cleaved caspase 3+ cells compared to GFP expression alone (data not shown). Dengue virus (DENV), a closely related member of the flaviviridae family, has not been linked to either microcephaly or deficits in NSC proliferation. In comparison, we examined DENV-NS2A, which shares 24.8% homology at the protein level with ZIKV-NS2A (data not shown) and presumably plays a similar role in flavivirus replication and assembly. Upon in utero electroporation to express DENV-NS2A, we did not observe any significant differences in percentages of EdU+ cells among all GFP+ cells, GFP+Pax6+ cells, or GFP+Tbr2+ IPCs, or the percentage of cleaved caspase 3+ cells, compared to GFP expression alone (data not shown). Therefore, ZIKV-NS2A, but not DENV-NS2A, impacts cortical neurogenesis in the embryonic mouse brain by reducing proliferation and promoting depletion of radial glia cells.

To address how ZIKV-NS2A directly interacts with the host machinery to impact NSC behavior, we again took an unbiased and systematic approach. We performed an in vitro protein microarray assay to identify human proteins that can bind to recombinant ZIKV-NS2A protein or DENV-NS2A protein. Among 20,240 full-length human proteins spotted on the protein microarray, which represent over 95% of protein encoding genes in the human genome, 143 and 47 proteins were identified as interacting proteins for ZIKV-NS2A and DENV-NS2A, respectively (data not shown). Among them, 45 proteins were shared between the two homologous NS2A proteins. Gene Ontology (GO) analysis of 143 ZIKV-NS2A interacting proteins revealed enrichment for multiple pathways, including extracellular exosome, cytoplasmic stress granule, and focal adhesion (data not shown). We further constructed a functional protein association network. We found that 83 ZIKV-NS2A interacting proteins formed a connected network ($P<4.91\times10^{-13}$), whereas the remaining 60 proteins are singletons (data not shown). Within the interaction network, 8 proteins (NME2, ARPC3, HSPB1, PABPC1, PTK2, VASP, PLEK and SMAD7) are related to cell adhesion (P=0.03). Among the singletons, NUMBL is also adhesion-related. Interestingly, most of these cell adhesion proteins (7 out 9) are ZIKV-specific (data not shown), raising the possibility that they may mediate some of the ZIKV-NS2A dependent effects.

Several of the adhesion-related proteins (PTK2, VASP, NUMBL, SMAD7, ARPC3) are linked to the adherens junction (AJ), which has been shown to be important to anchor radial glia cells and regulate their properties. A number of previous genetic manipulation studies have shown that disruption of AJ formation in radial glia cells can lead to their premature differentiation and depletion in the embryonic mouse cortex. To confirm that ZIKV-NS2A interacts with AJ complex components, we expressed ZIKV-NS2A in HEK293 cells and performed co-immunoprecipitation analysis. ZIKV-NS2A was detected in the same complex with multiple AJ components, including N-Cadherin, ZO-1, p-Catenin, SMAD7, and NUMBL. Importantly, infection of cultured NSCs derived from E11.5 mouse cortex directly with ZIKV led to reduced protein levels of several AJ components, including ZO-1, p-Catenin, SMAD7, and NUMBL. Similar reduced protein expression of these AJ components was observed in mouse NSCs expressing ZIKV-NS2A. The mRNA levels of most of these genes were not reduced in mouse NSCs upon ZIKV infection or ZIKV-NS2A expression, suggesting a post-transcriptional regulation mechanism. It is known that some AJ components are pre-assembled in the endoplasmic reticulum before they are delivered to the cell membrane to form AJ. As expected, immunostaining showed that both ZIKV-NS2A and DENV-NS2A were colocalized with an endoplasmic reticulum marker (data not shown). These findings raised the possibility that ZIKV-NS2A interaction with AJ complex components leads to their depletion and deficits in AJ formation. Indeed, immunostaining of p-Catenin, PKCA, or ZO-1 reveled deficits in AJ formation upon expression of ZIKV-NS2A, but not DENV-NS2A (data not shown). We also observed disorganization of radial glia fiber scaffolding and ventricular protrusions (data not shown) upon ZIKV-NS2A expression.

Finally, to determine whether ZIKV-NS2A dysregulates human cortical neurogenesis, we used the recently established human induced pluripotent stem cell (iPSC)-derived forebrain organoid model of the present disclosure. We co-expressed ZIKV-NS2A and GFP in ventricular radial glia cells in day 45 forebrain organoids by electroporation and 3 days later pulsed with EdU (10 μM) for 1 hour (data not shown). At day 3 after electroporation (45+3), expression of ZIKV-NS2A, but not DENV-NS2A, resulted in reduced percentages of EdU+ cells among all GFP+ cells or GFP+PAX6+ cells, or Ki67+ cells among all GFP+ cells, compared to GFP expression alone within the ventricular structures (data not shown). Furthermore, immunostaining for AJ marker PKCA, revealed disrupted AJ formation in ZIKV-NS2A expressing regions, resulting in discontinuous AJ at the ventricular surface (data not shown). In many cases, we also observed disruption of ventricular organization upon expression of ZIKV-NS2A, but not DENV-NS2A (data not shown). ZIKV-NS2A-induced disruption of ventricular organization became more pronounced when we analyzed organoids 7 days after electroporation (45+7), as the majority of GFP+PAX6+ cells lost their radial morphologies (data not shown). These results are reminiscent of a recent observation of loss of AJ formation, ventricular protrusions and disorganized radial glia scaffolding in postmortem forebrain tissue of the first reported ZIKV-infected microcephalic fetus from an infected mother.

The current epidemic ZIKV outbreak and associated microcephaly represents a serious public health challenge. Understanding mechanisms underlying ZIKV pathogenesis in the developing mammalian brain may reveal potential targets for anti-ZIKV and neuroprotective therapeutic interventions. Our systematic functional screen of ZIKV-encoded proteins led to the identification, for the first time, of an in vivo mechanism and a direct link of a ZIKV component to specific host machinery that may explain, at least in part, ZIKV-induced microcephaly. Deficits in AJ formation have been shown to lead to aberrant niche signaling that impacts cortical neurogenesis. Our finding does not rule out the possibility that ZIKV-NS2A may directly interact with other host molecules to regulate NSC behavior. Our databases of NS2A protein-protein interaction networks across the human proteome provides a rich resource for future exploration. For example, one ZIKV-NS2A interacting protein CEP63 itself is encoded by a microcephaly gene and belongs to the centrosomal protein family, many of which are encoded by recessive primary microcephaly genes. This global protein interactome databases may also be useful for understanding ZIKV/DENV replication and assembly to identify therapeutic targets. It is possible that other ZIKV components, including both ZIKV encoded proteins (e.g., ZIKV-C) and noncoding RNAs, may also contribute to the microcephaly phenotype observed in human fetus and in animal models.

Analogous to the contribution of studying v-Src encoded by Rous sarcoma virus to our current knowledge of cancer and related basic cell biology, ZIKV-induced microcephaly also provides an opportunity and an entry point to understand normal human brain development, about which we know little, largely because of a lack of experimental model systems. Our study using brain organoids provides one of the first examples and a quantitative platform to address basic mechanism regulating human neurogenesis.

Material and Methods

DNA Constructs

To clone ZIKV- and DENV-encoded open reading frames (ORFs), ZIKV MR766 (African strain) and DENV-1 (Hawaiian strain) were used to infect mosquito cells. One μg of total RNA was converted to cDNA using Superscript™ III (Thermo Fisher Scientific) for PCR templates. The viral ORFs were constructed by RT-PCR-based cloning from cDNA into the Gateway Entry vector system. Primer sets were designed for amplifying the full-length ORFs and attBI and attB2 sequences at the 5'-ends of each primer were added to clone PCR amplicon into Gateway Entry vector pDONR221 (Thermo Fisher Scientific) by Gateway recombination. Using the expression pEGH-A vector for expression and purification of N-terminal GST fusion protein, a stop codon (TAA) was added between attB2- and the gene specific reverse primer-sequences in all primers. Subcloning of NS2A ORFs were performed using Gateway recombination reactions. All entry clones were verified to be without any mutations at the amino acid sequences of all viral proteins by comparing to reference genome sequences of each viral strain. To express and purify individual viral proteins, sequence-verified Entry clones were cloned into a yeast expression vector pEGH-A. Verified clones were transformed to yeast strain Y258 that expresses GST fusion proteins under the control of the galactose-inducible GAL1 promoter.

To construct mammalian expression vectors under the control of the human Ubiquitin C promoter, sequence-verified entry clones were cloned into a lentiviral destination vector pCWX-R4-DEST-R2-PG (Addgene plasmid: 45957) by Gateway recombination reactions with pENTR-L4-Ubi-L1R (Addgene plasmid: 45959). To generate HA-tagged ZIKV- and DENV-NS2A expression vectors, the entry clones were amplified by PCR using 5' primers with attB1 sequence and 3' primers with HA-attB2 sequence and reinserted into pDONR221 and pCWX-R4-DEST-R2-PG by the same Gateway recombination, to fuse HA sequence into C-terminal of NS2A ORFs. All the final constructs were sequenced to confirm complete correspondence with original ORF sequences.

In Utero Electroporation and Analysis of Cortical Neurogenesis

In utero electroporation was performed mainly as described previously. In brief, timed-pregnant CD1 mice (Charles River Laboratory) at E14.5 were anesthetized and the uterine horns were exposed and approximately 1 to 2 μl of plasmid DNA, 0.5 μg/μl pCAG-GFP (Addgene plasmid: 11150)+2.5 μg/μl a ZIKV ORF expression vector or an empty lentiviral vector, was injected manually into the lateral ventricles of the embryos using a calibrated micropipette. Five pulses (40 V, 50 ms in duration with a 950 ms interval) were delivered across the uterus with two 5 mm electrode paddles (CUY650-5, Nepa Gene) positioned on either side of the head by a square wave electroporator (CUY21SC, Nepa Gene). After electroporation, the uterus was placed back in the abdominal cavity and the wound was sutured. Mouse embryos were injected with EdU (150 mg/kg of body weight, Thermo Fisher Scientific) 2 hr before sacrifice at E17.5.

For quantitative analysis of electroporated neocortices, only GFP+ cells localized within the dorso-lateral cortex were examined. 3×3 tiled images were obtained to cover the electroporated region of each coronal section with a 20× or 40× objective by scanning microscope (Zeiss™ LSM 800) and compared with equivalent sections in littermate counterparts. Quantifications were performed using Imaris™ software (Bitplane). All animal procedures were performed in accordance with the protocol approved by the Johns Hopkins Institutional Animal Care and Use Committee.

Immunohistology and Confocal Imaging

For immunostaining of tissue sections, brains of embryos were fixed with 4% paraformaldehyde in PBS overnight at 4° C. as previously described. Brains were cryoprotected in 30% sucrose in PBS, embedded in OCT compound, and sectioned coronally (20 μm-thickness) on a Leica CM3050S cryostat. For immunostaining of HEK293 cells, cells were fixed with 4% PFA in PBS for 20 min at 4° C. Brain sections and cells were blocked and permeabilized with the blocking solution (5% normal donkey serum, 3% Bovine serum albumin and 0.1% Triton X-100 in PBS) for 1 hr at room temperature, followed by incubation with primary antibodies diluted in the blocking solution at 4° C. overnight. After washing, secondary antibodies diluted in blocking solution were applied to the sections for 1 hr at room temperature. Nuclei were visualized by incubating for 10 min with 0.1 mg/ml 4,6-diamidino-2-phenylindole (DAPI; Sigma-Aldrich) in PBS. Stained sections were mounted with Pro- Long™ Gold antifade reagents (Thermo Fisher Scientific) and analyzed. All the antibodies and working concentrations used are listed in Table 51.

NS2A Binding Assays on HuProt Arrays and Data Analysis

NS2A proteins were expressed as GST fusions in the budding yeast, and purified using glutathione sepharose affinity chromatography, as described previously. On day one, each yeast strain containing the NS2A construct was inoculated in SC-URA media including glucose at 30° C., 200 rpm, overnight. On day two, primary seed cultures were inoculated in two 16 mL of SC-URA media including raffinose and incubated at 30° C., 90 rpm, overnight. On day three, the expression of individual viral proteins were induced by adding final 2% galactose to yeast cultures when the culture reached O.D. 0.9. Induced yeast cells were harvested, after 6 hr incubation, and stored at −80° C. until the protein purification. For initial protein purification step, Zirconia beads and lysis buffer including protease inhibitor cocktail (Roche) and reducing agent were immediately added to frozen pellets and yeast cells were mechanically lysed. Supernatant were incubated with glutathione beads in fresh plates for 2 hr at 4° C. The mixtures of glutathione beads and individual viral proteins were washed each three times under both high (500 mM NaCl)- and low (100 mM NaCl)-salt washing buffer including protease inhibitor and reducing agent. For quality control of eluted proteins, all purified proteins were examined by SimplyBlue stain or anti-GST Western blot analysis.

Each purified ZIKV- and DENV-NS2A protein was fluorescently labeled with Cy5-NHS ester using a commercial kit (GE Life Science) and diluted to a final concentration of 10 ng/4 in 200 μL of 1×TBST with 2% bSa. HuProt arrays (version III), comprised of 20,240 individually purified human proteins in full-length, were first blocked with 1×TBST with 2% BSA at room temperature for 2 hr. Each labeled NS2A protein was incubated on the blocked HuProt arrays in duplicate at RT for 1 hr. After three 15-min washes with 1×TBST, the HuProt arrays were briefly rinsed with water and spun to dryness. After scanning the HuProt arrays with a microarray scanner (GenePix™ 4000B), the NS2A binding signals were acquired and analyzed using the GenePix™ software.

GenePix™ 6.1 was used to align the spot-calling grid. For each protein spot, the median values of foreground (Fij and background (Bij intensities at site (ij) on the microarray were extracted, respectively. The binding intensity (Rij) of each protein spot was defined as Fij/Bij. Since each protein is printed in duplicate on each microarray, Rij was averaged for the duplicate as R'ij. Using the similar method in our previous study, the Z-score of each probe was calculated based on the distribution of R'ij, $$Z_{ij} = \frac{R'ij - \overline{N}}{SD}.$$

A stringent cutoff (Z>10) was used to determine the positive hit list.

For protein-protein interaction analysis, the functional protein association network was constructed using STRING™ 10.0 database (on the World Wide Web at string-db.org. The protein-protein interactions were obtained with the default parameters (confidence score 0.4). The P value of association enrichment was also given by the database taking all proteins in the protein microarray as background. The association network was generated using Cytoscape™ 3.2.1.

Gene ontology enrichment analyses for NS2A binding proteins were performed using DAVID™ 6.8 (on the World Wide Web at david.ncifcrf.gov/).

Cell Culture, Transfection and Infection

HEK293 cells were cultured in DMEM containing 10% FBS (Hyclone, Logan, Utah, USA), 4 mM L-glutamine (Gibco BRL), 100 IU/ml penicillin (Gibco BRL) and 100 μg/ml streptomycin (Gibco BRL). For co-immunoprecipitation experiments, HEK293 cells were transfected with control and ZIKV NS2A expressing constructs with Lipofectamine 2000 (Thermo Fisher Scientific) and collected after 48 hr.

Mouse NSCs were isolated from E11.5 CD1 mouse embryo and cultured in Neurobasal medium (Gibco BRL) containing 20 ng/ml FGF2, 20 ng/ml EGF, 5 mg/ml heparin, 2% B27 (v/v, Gibco BRL), 4 mM L-glutamine as previously described. High titer lentivirus were produced from HEK293 cells and used to infect mouse NSCs in the presence of 4 μg/ml polybrene (Milipore). Mouse NSC lysates were collected on 4 days after control and ZIKV-NS2A expressing lentivirus. ZIKV were prepared and infected as previously described. Mouse NSCs were infected with ZIKV at MOI 0.08 for 64 hr and collected for Western blotting and quantitative PCR analysis as previously described.

Co-immunoprecipitation and Western Blot Analysis

For co-immunoprecipitation analysis, HEK293 cells were homogenized in the lysis buffer containing Phosphate-buffered saline (pH 7.4), 1.5% Triton-X™ 100, 1 mM Na3VO4, 1 mM NaF, 1 mM DTT, and protease inhibitor cocktails (Sigma-Aldrich). The lysates were incubated for 15 min on ice, sonicated and centrifuged for 15 min at 15,000*g 4° C. The supernatants were collected and immunoprecipitated with anti-HA magnetic beads (Thermo Fisher Scientific) for overnight at 4° C. The beads were thoroughly washed with lysis buffer, boiled with Laemmli Sample Buffer (Bio-Rad) and subjected to Western blot analysis. For Western blotting, samples were separated by 4-20% SDS-PAGE, transferred to nitrocellulose membranes (Bio-Rad), incubated with primary and secondary antibodies and visualized with SuperSignal™ West Dura Chemiluminescent Substrate (Thermo Fisher Scientific). Quantification of bands was performed using ImageJ™ software.

RNA Preparation and Quantitative PCR

For gene expression analysis, total RNA fraction was immediately isolated from cultured mouse NSC samples with RNeasy™ Mini Kit (Qiagen), treated with DNaseI and reverse-transcribed into the first-strand cDNA with SuperScript™ III (Thermo Fisher Scientific). cDNAs were used for SYBR-green based quantitative real-time PCR to measure the expression level of target genes with the comparative CT method (ABI).

The following primers were used for quantitative PCR.

```
Gapdh (forward:
5 - TCAACAGCAACTCCCACTCTTCCA -3 (SEQ ID NO: 1);
reverse:
5 - ACCCTGTTGCTGTAGCCGTATTCA -3 (SEQ ID NO: 2)).

Smad7 (forward:
5 - TCAAGAGGCTGTGTTGCTGT -3 (SEQ ID NO: 3);
reverse:
5 - CAGGCTCCAGAAGAAGTTGG -3 (SEQ ID NO: 4)).
```

```
Ctnnb 1 (β-Catenin) (forward:
5 - ACAGGGTGCTATTCCACGAC -3 (SEQ ID NO: 5);
reverse:
5 - CTGCACAAACAATGGAATGG -3 (SEQ ID NO: 6)).

Numbl (forward:
5 - TCCGTGAAGTCTGTCCTGTG -3 (SEQ ID NO: 7);
reverse:
5 - GCCTCTCACCAGAGTCCTTG -3 (SEQ ID NO: 8)).

Tjp1 (ZO-1) (forward:
5 - GGGCCATCTCAACTCCTGTA -3 (SEQ ID NO: 9);
reverse:
5 - AGAAGGGCTGACGGGTAAAT -3 (SEQ ID NO: 10)).

Cdh2 (N-Cadherin) (forward:
5 - GGGACAGGAACACTGCAAAT -3 (SEQ ID NO: 11);
reverse:
5 - CGGTTGATGGTCCAGTTTCTT -3 (SEQ ID NO: 12)).

ZIKV Ns2a (forward:
5 - GGCTACTTGTGGAGGGATCA -3 (SEQ ID NO: 13);
reverse:
5 - ACCCTCACAGCTGTCAATCC -3 (SEQ ID NO: 14)).
```

Forebrain Organoid Culture

Human iPSC lines from healthy subjects used in the current study have been fully characterized. Protocols for generation of forebrain organoids using the SpinΩ bioreactor were detailed previously. Briefly, human iPSCs were cultured in stem cell medium, consisting of DMEM:F12 (Invitrogen) supplemented with 20% Knockout™ Serum Replacer (Gibco), 1× Non-essential Amino Acids (Invitrogen), 1× Penicillin/Streptomycin (Invitrogen), 1×2-Mercaptoenthanol (Millipore), 1× Glutamax (Invitrogen), and 10 ng/ml FGF-2 (Peprotech) on irradiated CF1 mouse embryonic fibroblasts (Charles River). On day 1, iPSC colonies were detached by treatment of 1 mg/ml Collagenase Type IV (Invitrogen) for 1 hr and transferred to an Ultra-Low attachment 6-well plate (Corning Costar), containing 3 ml of stem cell medium (without FGF-2), plus 2 μM Dorsomorphin (Sigma) and 2 μM A83-01 (Tocris). On days 5-6, half of the medium was replaced with induction medium consisting of DMEM:F12, 1× N2 Supplement (Invitrogen), 1× Penicillin/Streptomycin, 1× Non-essential Amino Acids, 1× Glutamax, 1 μM CHIR99021 (Cellagentech), and 1 μM SB-431542 (Cellagentech). On day 7, organoids were embedded in Matrigel (Corning) and continued to grow in induction medium for 6 more days. On day 14, embedded organoids were mechanically dissociated from Matrigel and transferred to each well of a 12-well spinning bioreactor (SpinΩ; the culture device of the present invention as shown in FIGS. 1-11) containing differentiation medium, consisting of DMEM:F12, 1×N2 and B27 Supplements (Invitrogen), 1× Penicillin/Streptomycin, 1×2-Mercaptoenthanol, 1× Non-essential Amino Acids, 2.5 μg/ml Insulin (Sigma).

Forebrain Organoid Electroporation and Analysis

On day 45, forebrain organoids were transferred into PBS solution in 10 cm petri dish for electroporation. A mixture of 0.5 μl of plasmid DNA and 0.05% Fast green was injected into the ventricle-like cavity of neural tube structures in forebrain organoid using a calibrated micropipette. About 3-4 locations in one side of each forebrain organoids were targeted by the injection. The DNA-injected side of the organoid was placed toward the positive electrode in the middle of 5 mm gap of electrode paddles (CUY650-5, Nepa Gene). Five pulses (40 V, 50 ms in duration with a 950 ms interval) were delivered by a square wave electroporator (CUY21SC, Nepa Gene). After electroporation, organoids were transferred back to SpinΩ bioreactor for continuing culturing. On day 48 (45+3) or day 52 (45+7), organoids were pulsed by 10 μM EdU (ThermoFisher) for 1 hr by directly adding EdU into culture media and fixed for immunostaining analysis. The protocol for tissue preparation and immunohistochemistry was described previously.

For quantification after electroporation, randomly selected ventricular structures with electroporated "fan-shaped" regions pointing towards the pial surface, but not the interior of organoid, were imaged by confocal microscope (Zeiss' LSM 800). Among electroporated cells labelled by GFP, EdU+, Ki67+ or PAX6+ nuclei were counted using ImageJ™ software, and the effect from expression of different constructs (GFP, GFP+ZIKV-NS2A, or GFP+DENV-NS2A) was evaluated by the percentage of EdU+ or Ki67+ cells among total GFP+ or GFP+PAX6+ cells. Multiple organoids were quantified and Student's t-test was used for statistical analysis.

Example 4

Differentiation of Pluripotent Stem Cells into Medial Ganglionic Eminence and to Interneurons Protocol A: Differentiation of Pluripotent Stem Cells into Medial Ganglionic Eminence and to Interneurons

| Day | Short Instructions | Culture Condition | Media |
|---|---|---|---|
| 0 | 1. Detach Stem Cells for EB Generation<br>2. Suspend EBs in Ultra-Low Attachment Plates with A83+ Dorso-Enriched Media | Suspension | Survival Medium |
| 1 | Exchange Media for Induction Medium | Suspension | Induction Medium |
| 1-6 | Maintain in Induction Medium | Suspension | Induction Medium |
| 6 | Embed in Matrigel | Matrigel | Induction Medium |
| 6-13 | Maintain in Induction Medium | Spin | Induction Medium |
| 13 | 1. Resuspend in Spinning Culture<br>2. Exchange Media for Differentiation Medium | Spin | Differentiation Medium |
| 13-21 | Maintain in Differentiation Medium | Spin | Differentiation Medium |
| 21+ | Maintain in Maturation Medium | Spin | Maturation Medium |

Culture conditions indicated as "Spin" refer to culture in an apparatus as set forth in FIGS. 1-11.

Media Types are Provided as Follows:
1. Survival medium (day 0)
A83-01 (2 uM)
Dorsomorphine (2 uM)
Beta-mercaptoethanol (1×)
Heparin (10 ug/mL)
Glutamax (1×)
Non-essential amino acids (1×)
Knock-out serum replacement (20%)
DMEM/F12
2. Induction medium (days 1-13)
DMEM/F12
N2 supplement (1×)
Penicillin/Streptomycin (1×)
Heparin (10 ug/mL)
Non-essential amino acids (1×)
Glutamax (1×)
CHIR99021 (2 uM)
SB-431542 (1 uM)
Purmorphamine (1.5 uM)

3. Differentiation medium (days 13-21)
Neurobasal (Gibco)
Penicillin/Streptomycin (1×)
Beta-mercaptoethanol (1×)
B27 Supplement (1×)
Ascorbic acid (0.2 mM)
FGF8 (100 ng/mL)
4. Maturation medium (days 21+)
Neurobasal (Gibco)
Penicillin/Streptomycin (1×)
Beta-mercaptoethanol (1×)
B27 Supplement (1×)
Ascorbic acid (0.2 mM)
BDNF (Peptrotech) (20 ng/mL)
GDNF (Peprotech) (20 ng/mL)
TGF-beta (Peprotech) (1 ng/mL)
cAMP (Sigma) (0.5 mM)

Although the invention has been described with reference to the above examples, it will be understood that modifications and variations are encompassed within the spirit and scope of the invention. Accordingly, the invention is limited only by the following claims.

What is claimed is:

1. A method of cell culture comprising:
a) providing a cell culture system, the cell culture system comprising:
a first multiwell culture plate, the first multiwell culture plate having:
i) a base substrate having a plurality of culture wells; and
ii) a shaft operably associated with each culture well, each shaft being configured to mix media present in each culture well and having a gear adapted to operably associate with a gear on a shaft associated with an adjacent culture well;
a second multiwell culture plate, the second multiwell culture plate having:
i) a base substrate having a plurality of culture wells; and
ii) a shaft associated with each culture well, each shaft being configured to mix media present in each culture well and having a gear adapted to operably associate with a gear on a shaft associated with an adjacent culture well; and
a motor having a drive shaft in operable communication with the shaft gears of the first and second multiwell culture plates,
wherein rotation of the drive shaft causes rotation of each shaft of the first and second multiwell culture plates and mixing of the media in each culture well of the first and second multiwell culture plates, and
wherein the first and second multiwell culture plates are in a stacked configuration; and b) culturing a cell in a culture well of the first or second multiwell culture plate in culture media under conditions suitable for cell culture, wherein the conditions comprise mixing of the cell culture via actuation of the motor, thereby culturing the cell.

2. The method of cell culture of claim 1, wherein the culture media is mixed at a speed suitable to suspend cells within the culture wells.

3. The method of cell culture of claim 2, wherein the culture media is mixed at a shaft speed of between about 30-125 RPM.

4. The method of cell culture of claim 1, wherein the cell is a stem cell.

5. The method of cell culture of claim 4, wherein the cell is an induced pluripotent stem cell (iPSC) or an embryonic stem cell (ESC).

6. The method of cell culture of claim 1, further comprising introducing a biological agent into the culture media and detecting a cellular response.

7. The method of claim 6, wherein the biological agent is a virus.

8. The method of cell culture of claim 1, further comprising introducing an agent into the culture media that promotes cellular differentiation.

9. A method of producing organoids comprising:
a) providing a cell culture system, the cell culture system comprising:
a first multiwell culture plate, the first multiwell culture plate having:
i) a base substrate having a plurality of culture wells; and ii) a shaft operably associated with each culture well, each shaft being configured to mix media present in each culture well and having a gear adapted to operably associate with a gear on a shaft associated with an adjacent culture well;
a second multiwell culture plate, the second multiwell culture plate having:
i) a base substrate having a plurality of culture wells; and
ii) a shaft associated with each culture well, each shaft being configured to mix media present in each culture well and having a gear adapted to operably associate with a gear on a shaft associated with an adjacent culture well; and
a motor having a drive shaft in operable communication with the shaft gears of the first and second multiwell culture plates,
wherein rotation of the drive shaft causes rotation of each shaft of the first and second multiwell culture plates and mixing of the media in each culture well of the first and second multiwell culture plates, and
wherein the first and second multiwell culture plates are in a stacked configuration;
b) culturing a cell in a culture well of the first or second multiwell culture plate in culture media under conditions suitable for cell culture, wherein the conditions comprise mixing of the cell culture via actuation of the motor; and
c) optionally harvesting organoids from the culture well; thereby producing organoids.

10. The method of claim 9, wherein the culture media is mixed at a speed suitable to suspend cells within the culture well.

11. The method of claim 10, wherein the culture media is mixed at a shaft speed of between about 30-125 RPM.

12. The method of claim 9, wherein the cell is a stem cell.

13. The method of claim 12, wherein the cell is an induced pluripotent stem cell (iPSC) or an embryonic stem cell (ESC).

14. The method of claim 9, wherein the organoids comprise brain tissue or brain tissue precursors.

15. The method of claim 14, wherein the brain tissue or precursors are related to cerebral cortex, midbrain or hypothalamus tissue.

16. The method of claim 14, wherein the brain tissue or precursors are forebrain-specific organoids.

17. The method of claim 9, further comprising introducing a biological agent into the culture media and detecting a cellular response.

18. The method of claim 17, wherein the biological agent is a virus.

19. The method of claim 9, further comprising introducing an agent into the culture media that promotes cellular differentiation.

* * * * *